(12) United States Patent
Heckmeier et al.

(10) Patent No.: US 6,929,832 B2
(45) Date of Patent: Aug. 16, 2005

(54) LIQUID-CRYSTAL MEDIUM, AND ELECTRO-OPTICAL DISPLAY CONTAINING THE LIQUID-CRYSTAL MEDIUM

(75) Inventors: Michael Heckmeier, Bensheim (DE); Brigitte Schuler, Haibach (DE); Kazuaki Tarumi, Seeheim (DE); Marcus Reuter, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 92 days.

(21) Appl. No.: 09/465,006

(22) Filed: Dec. 16, 1999

(65) Prior Publication Data
US 2003/0134055 A1 Jul. 17, 2003

(30) Foreign Application Priority Data

| Mar. 3, 1999 | (DE) | 199 09 238 |
| Apr. 12, 1999 | (DE) | 199 16 496 |
| Aug. 27, 1999 | (DE) | 199 40 655 |

(51) Int. Cl.$^7$ .................. C09K 19/34; C09K 19/30; C09K 19/12
(52) U.S. Cl. .............. 428/1.1; 252/299.61; 252/299.63; 252/299.66
(58) Field of Search ................ 252/299.61, 299.63, 252/299.66; 428/1.1

(56) References Cited

U.S. PATENT DOCUMENTS

| 5,520,846 A | * | 5/1996 | Plach et al. ............ 252/299.63 |
| 5,807,500 A | * | 9/1998 | Bremer et al. ......... 252/299.66 |
| 5,827,450 A | * | 10/1998 | Numata et al. ........ 252/299.63 |
| 5,868,962 A | * | 2/1999 | Rieger et al. .......... 252/299.63 |
| 5,883,686 A | * | 3/1999 | Leenhouts et al. .......... 349/177 |
| 5,948,318 A | * | 9/1999 | Miyazawa et al. ..... 252/299.63 |
| 5,965,060 A | * | 10/1999 | Tarumi et al. ......... 252/299.63 |
| 6,056,894 A | * | 5/2000 | Hirschmann et al. .. 252/299.63 |
| 6,066,268 A | * | 5/2000 | Ichinose et al. ....... 252/299.63 |
| 6,083,573 A | * | 7/2000 | Tarumi et al. ............... 428/1.1 |
| 6,117,360 A | * | 9/2000 | Miyazawa et al. ..... 252/299.63 |
| 6,210,761 B1 | * | 4/2001 | Kondo et al. ................ 428/1.1 |
| 6,638,581 B2 | * | 10/2003 | Heckmeier et al. .......... 428/1.1 |

FOREIGN PATENT DOCUMENTS

| DE | 19521483 | * | 1/1996 |
| WO | 98/23563 | * | 6/1998 |

OTHER PUBLICATIONS

EP abstract of WO 9621881, 1996.*

* cited by examiner

Primary Examiner—Shean C. Wu
(74) Attorney, Agent, or Firm—Millen, White, Zelano, Branigan, P.C.

(57) ABSTRACT

AMLCDs containing a liquid-crystal medium which comprises a) at least one compound of the formula I and b) at least one compound of the formula II

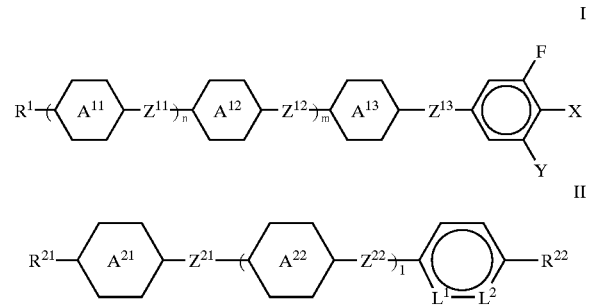

where the various parameters are as defined in the text, and to these liquid-crystal media and to their use in electro-optical displays.

26 Claims, 1 Drawing Sheet

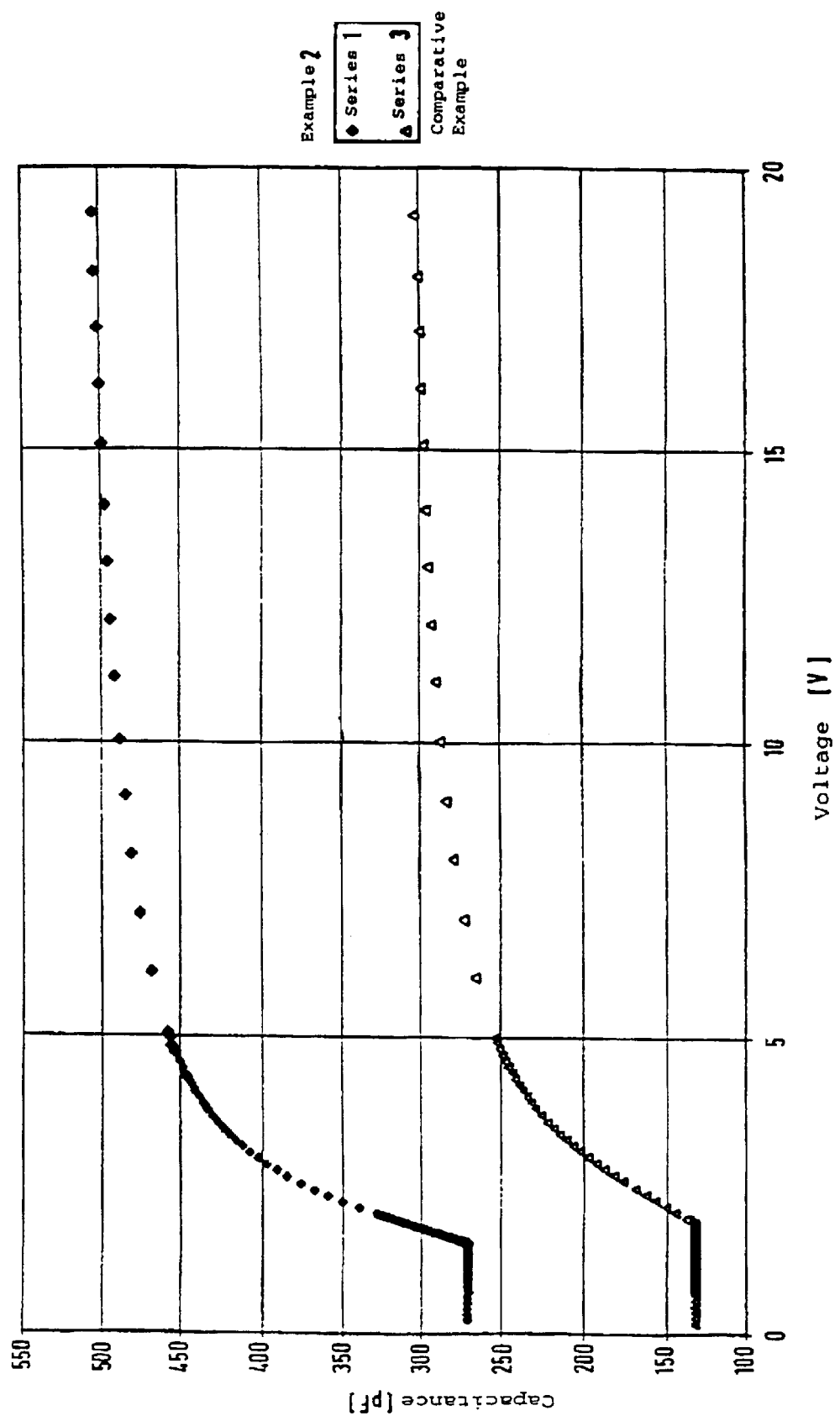

LIQUID-CRYSTAL MEDIUM, AND ELECTRO-OPTICAL DISPLAY CONTAINING THE LIQUID-CRYSTAL MEDIUM

The present invention relates to active matrix-addressed liquid-crystal displays (AMDs or AMLCDs), in particular those which use an active matrix of thin-film transistors (TFTs) or varistors. In addition, the present application relates to liquid-crystal media for use in such displays. Such AMDs can use various active electronic switching elements. The most widespread are displays using three-pole switching elements. These are also preferred in the present invention. Examples of such three-pole switching elements are MOS (metal oxide silicon) transistors and the abovementioned TFTs or varistors. In the case of TFTs, various semiconductor materials, predominantly silicon or cadmium gelenside, are used. In particular, polycrystalline silicon or amorphous silicon is used. In contrast to the three-pole electronic switching elements, matrices of 2-pole switching elements, such as, for example, MIM (metal insulator metal) diodes, ring diodes or back-to-back diodes, can be employed in AMDs. However, these are, as also explained in greater detail below, not preferred owing to the inferior electro-optical properties achieved by the AMDs.

In liquid-crystal displays of this type, the liquid crystals are used as dielectrics whose optical properties change reversibly on application of an electric voltage. Electro-optical displays which use liquid crystals as media are known to the person skilled in the art. These liquid-crystal displays use various electro-optical effects. The most common of these are the TN effect (twisted nematic, having a nematic structure which is twisted by about 90°), the STN effect (supertwisted nematic) and the SBE effect (supertwisted birefringence—effect). In these and similar electro-optical effects, liquid-crystalline media of positive dielectric anisotropy ($\Delta\epsilon$) are used.

Since the operating voltage should be kept as low as possible in displays in general, including in displays using these effects, use is made of liquid-crystal media of large dielectric anisotropy which are generally composed predominantly of dielectrically positive liquid-crystal compounds and contain at most smaller/lower proportions of dielectrically neutral compounds.

Besides these electro-optical effects, which require liquid-crystal media of positive dielectric anisotropy, there are other electro-optical effects which use liquid-crystal media of negative dielectric anisotropy, such as, for example, the ECB effect (electrically controlled birefringence) and its sub-forms DAP (deformation of aligned phases), VAN (vertically aligned nematics) and CSH (colour super homeotropics).

The IPS effect (in-plane switching), which has been increasingly used recently, can use both dielectrically positive and dielectrically negative liquid-crystal media, similarly to guest/host displays, which, depending on the display mode used, can use dyes either in dielectrically positive or in dielectrically negative media.

The liquid-crystal media employed in the abovementioned liquid-crystal displays and all liquid-crystal displays utilizing similar effects generally consist predominantly and usually even very substantially of liquid-crystal compounds having the corresponding dielectric anisotropy, i.e. compounds of positive dielectric anisotropy in the case of dielectrically positive media and compounds of negative dielectric anisotropy in the case of dielectrically negative media.

In the respective types of media (dielectrically positive or dielectrically negative), at best significant amounts of dielectrically neutral liquid-crystal compounds are typically employed, since in general the liquid-crystal displays must have the lowest possible addressing voltages. For this reason, liquid-crystal compounds having the opposite sign of the dielectric anisotropy to the dielectric anisotropy of the medium are generally employed extremely sparingly or not at all.

An exception is formed here by liquid-crystalline media for MIM displays (metal insulator metal) [J. G. Simmons, Phys. Rev. Vol. 155 No. 3, pp. 657–660; K. Niwa et al., SID 84 Digest, pp. 304–307, June 1984], in which the liquid-crystal media are addressed on an active matrix of thin film transistors (TFD, thin film diodes). In this type of addressing, which utilizes the non-linear characteristic line of diode switching, a storage capacitor cannot be charged together with the electrodes of the liquid-crystal display elements (pixels), in contrast to TFT displays. Thus, in order to minimize the effect of voltage drop during the addressing cycle, the highest possible base value of the dielectric constant is necessary. In dielectrically positive media, as employed, for example, in MIM-TN displays, the dielectric constant perpendicular to the molecular axis ($\epsilon_\perp$) must thus be as large as possible, since it determines the base capacity of the pixel. To this end, as in WO 93/01253, EP 0 663 502 and DE 195 21 483, compounds of negative dielectric anisotropy are used in the dielectrically positive liquid-crystal media, besides dielectrically positive compounds.

During charging of the electrodes of the pixel by TFT addressing, the voltage present is shifted by a DC offset voltage ($\Delta V$) by the parasitic capacitance between the gate and source of the TFT. $\Delta V$ is proportional to the inverse value of the pixel capacitance ($C_{pix}$). It can be seen from this that if the pixel capacitance is relatively large both in the on and also in the partly off and in particular in the semi-off state, the undesired effect is reduced and $\Delta V$ becomes smaller.

EP 0 394 419 proposes dielectrically positive liquid-crystal media for active matrix displays based on dielectrically neutral and dielectrically positive liquid-crystal compounds, which may optionally contain dielectrically negative compounds. Although EP 0 394 419 proposes a number of examples of dielectrically negative liquid-crystal compounds, this patent application gives, with Example 22, only one of a total of 72 examples which comprises a dielectrically negative compound, and even here only in a very small proportion of 4%.

The liquid-crystal media of the prior art have relatively low low-temperature stabilities. Thus, the nematic phases frequently extend only down to −20° C. and in some cases even only down to 0° C. In addition, the threshold voltages ($V_{10}$) are also simultaneously relatively high, usually even greater than 2 V. The majority of the liquid-crystal media of the prior art have relatively large values for $\Delta n$, frequently greater than 0.10, in some cases even significantly greater than 0.10, and predominantly greater than 0.09. However, such large $\Delta n$ values are not particularly advantageous for TN displays operated at the first Gooch and Tarry transmission minimum, i.e. at an optical retardation d·$\Delta n$ of approximately 0.5 µm, as employed in order to achieve good, low viewing-angle dependence of the contrast (DE 30 22 818). Such large $\Delta n$ values require very small layer thicknesses to be achieved, which, although favourable for the response times observed, result, however, in low production yields.

There thus was and is a great demand for liquid-crystal media which do not have the disadvantages of the media of the prior art, or at least do so to a significantly reduced extent, and which simultaneously have reduced cross-talk between adjacent pixels, in particular between on pixels and adjacent off pixels.

Furthermore, so-called flicker is observed in some active matrix addressed displays. This effect is observed both in displays in TN mode and also, in particular, in those VAN mode. This interfering effect is attributed, at least in part, to the voltage offset AV of the voltage present on the LC cell, which is itself caused by the varying polarity of the drain voltage at the transistors of the active matrix.

This is achieved by using the liquid-crystal media according to the invention, which enable a small difference in the capacitances of adjacent on and off pixels.

BRIEF DESCRIPTION OF DRAWING

FIG. 1 shows the capacitance of test cells filled with liquid-crystal mixtures as a function of the applied voltage.

The liquid-crystal media according to the invention comprise a) one or more dielectrically positive compound(s) of the formula I

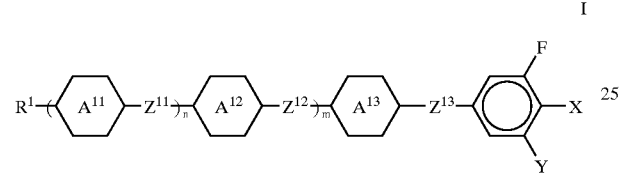

in which $R^1$ is alkyl or alkoxy having 1 to 7 carbon atoms, alkoxyalkyl, alkenyl or alkenyloxy having 2 to 7 carbon atoms, $Z^{11}$, $Z^{12}$ and $Z^{13}$ are each, independently of one another, $-CH_2-CH_2-$, $-CH=CH-$, $-C\equiv C-$, $-COO-$ or a single bond,

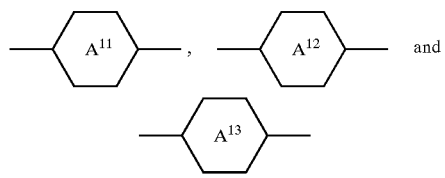

are each, independently of one another,

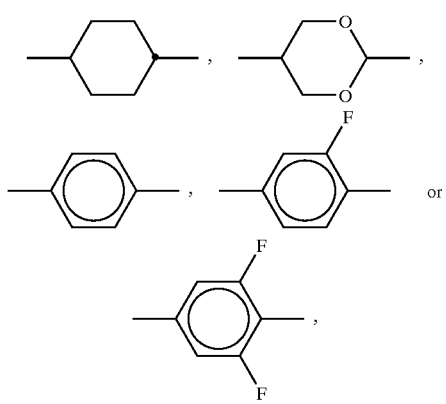

X is F, $OCF_2H$ or $OF_3$, where, in the case where X=F or $OCF_2H$, Y is F, and in the case where X=$OCF_3$, Y is H or F, and n and m are each, independently of one another, 0 or 1;

b) one or more dielectrically negative compound(s) of the formula II

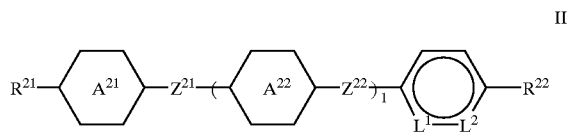

in which $R^{21}$ and $R^{22}$ are each, independently of one another, as defined for $R^1$ under the formula I, $Z^{21}$ and $Z^{22}$ are each, independently of one another, as defined for $Z^{11}$ above under the formula I,

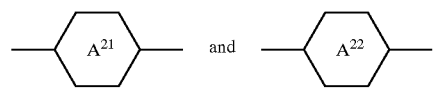

are each, independently of one another,

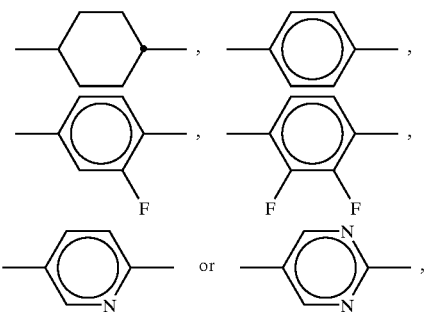

$L^1$ and $L^2$ are both C—F or one of the two is N and the other is C—F, and l is 0 or 1;

X is preferably F or $OCF_3$, particularly preferably F; $R^{22}$ is preferably alkyl or alkoxy having 1–7 carbon atoms, and $L^1$ and $L^2$ are preferably both C—F.

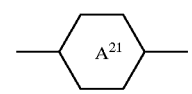

is particularly preferably

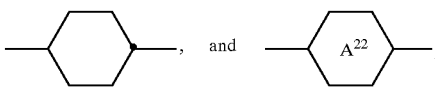

if present, is particularly preferably

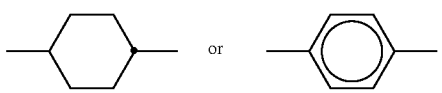

and optionally c) one or more dielectrically neutral compound(s) of the formula III

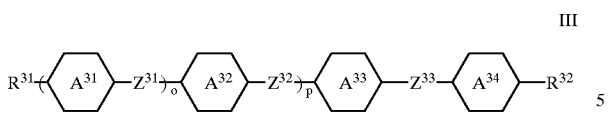   III in which
$R^{31}$ and $R^{32}$ are each, independently of one another, as defined for $R^1$ above under the formula I, and
$Z^{31}$, $Z^{32}$ and $Z^{33}$ are each, independently of one another, —CH$_2$CH$_2$—, —CH=CH—, —CH$_2$O—, —OCH$_2$—, —CF$_2$O—, —OCF$_2$—, —COO— or a single bond, and, if desired, one of $Z^{31}$, $Z^{32}$ and $Z^{33}$ is —CF$_2$CF$_2$—,

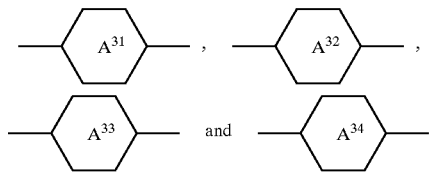

are each, independently of one another,

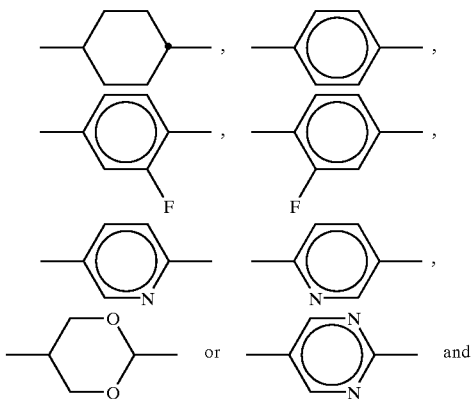

o, and p, independently of one another, are 0 or 1, but preferably
$R^{31}$ and $R^{32}$ are each, independently of one another, alkyl or alkoxy having 1–5 carbon atoms or alkenyl having 2–5 carbon atoms,

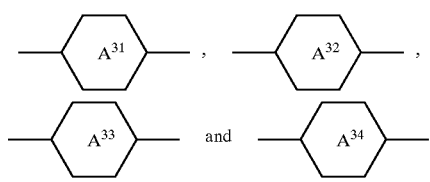

are each, independently of one another,

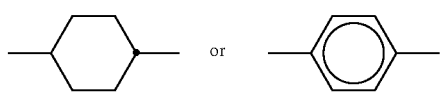

and very particularly preferably at least two of these rings are

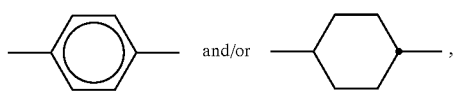

where two adjacent rings are very particularly preferably directly linked and are preferably

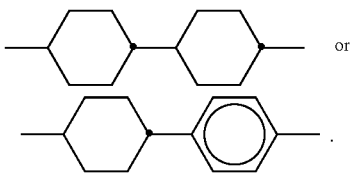

The liquid-crystal media preferably comprise one or more compounds selected from the group of compounds of the formulae I1 to I4:

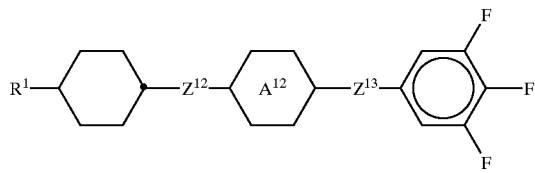   I1

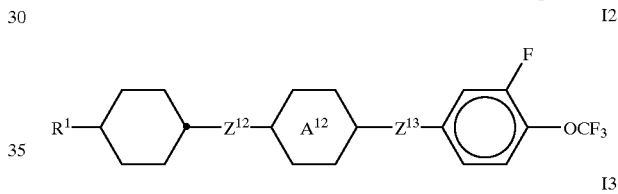   I2

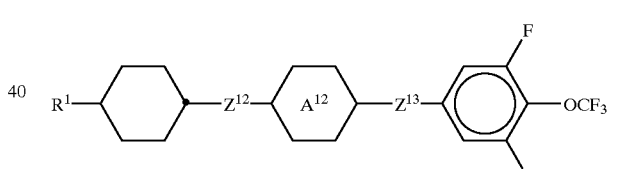   I3

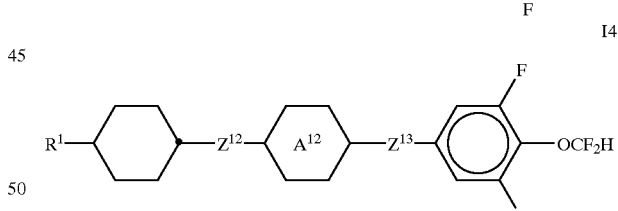   I4 in which $R^1$, $Z^{12}$, $Z^{13}$ and

are as defined above for formula I, but preferably
$R^1$ is alkyl having 1–7 carbon atoms or alkenyl having 2–7 carbon atoms, preferably vinyl or 1E-alkenyl,
one of $Z^{12}$ and $Z^{13}$ is a single bond and the other is —CH$_2$CH$_2$—, —COO— or a single bond, and

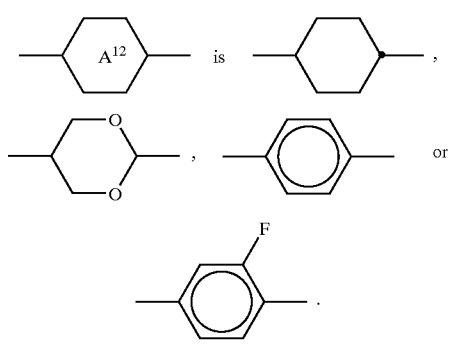
The liquid-crystal media particularly preferably comprise one or more compounds selected from the group of compounds of the formulae I1a to I1e, I2a to I2e, I3a to I3e and I4a to I4e:
I1a
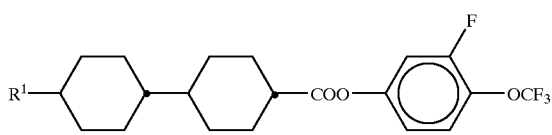
I1b
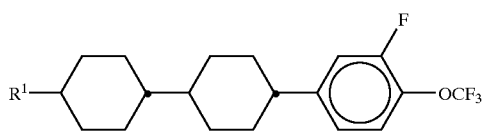
I1c
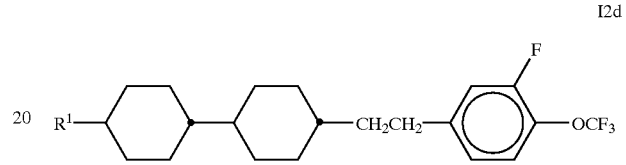
I1d
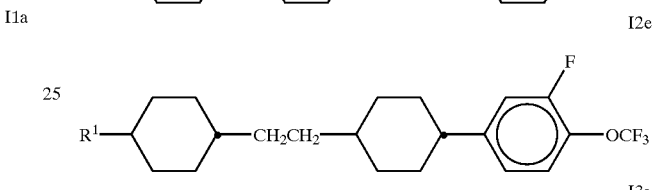
I1e
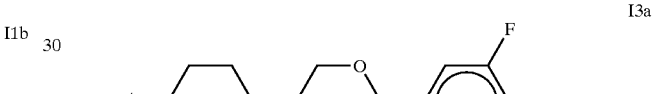
I2a
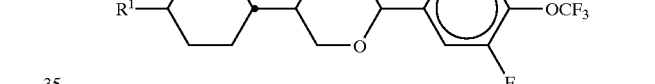
I2b
I2c
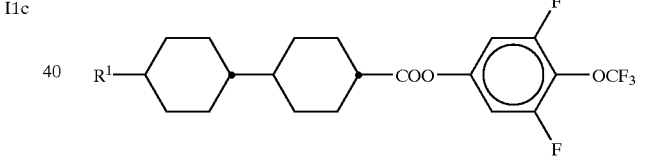
I2d
I2e
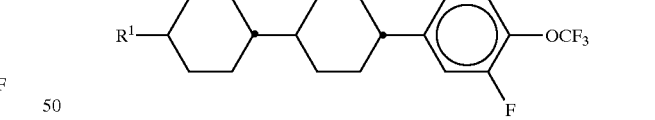
I3a
I3b
I3c
I3d
I3e
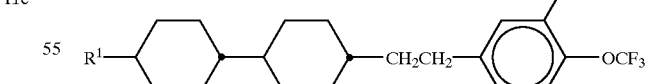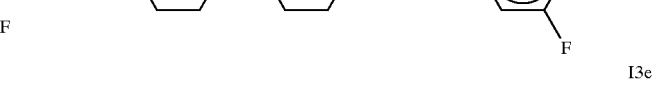

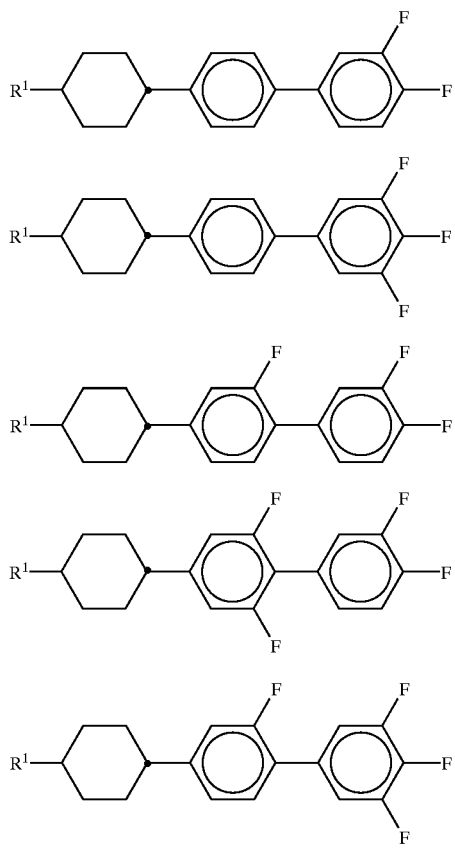

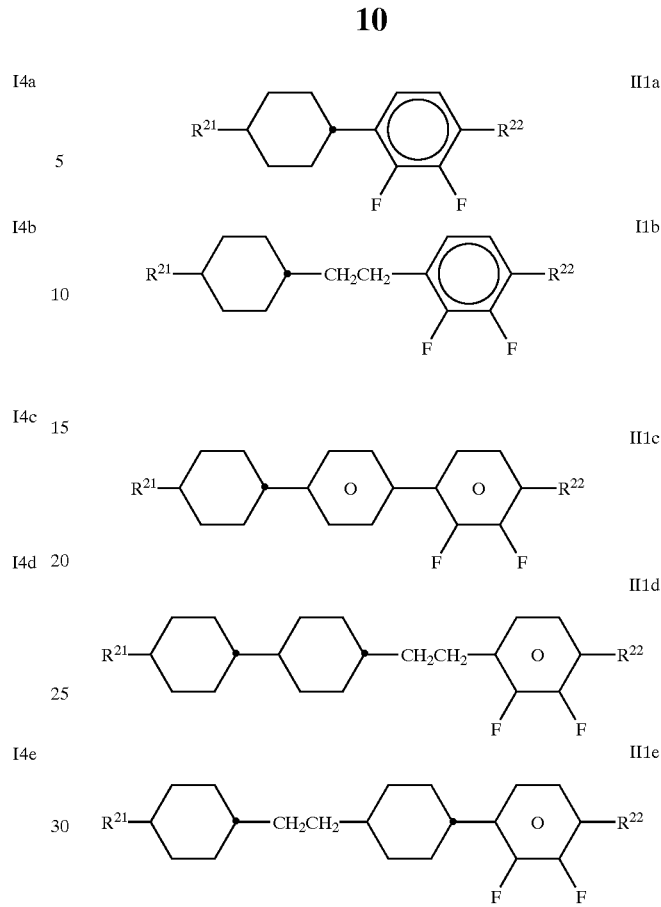

in which $R^1$ is as defined above under the formula I and is preferably as defined above under the formula I1. $R^1$ is in particular ethyl, n-propyl, n-butyl or n-pentyl.

The liquid-crystal medium preferably comprises one or more compounds of the formula II1

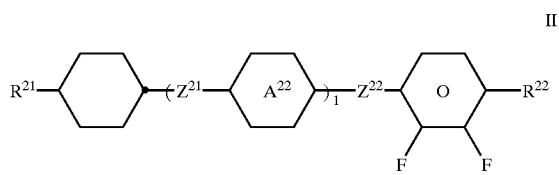

in which $R^{21}$, $R^{22}$, $Z^{21}$, $Z^{22}$,

and 1 are each as defined above under the formula II. $R^{21}$ is preferably alkyl having 1–5 carbon atoms, $R^{21}$ is preferably alkyl or alkoxy, each having 1 to 5 carbon atoms, and $Z^{22}$ and $Z^{21}$, if present, are preferably a single bond.

The liquid-crystal media particularly preferably comprise one or more compounds selected from the group of compounds of the formulae II1a to II1e:

in which $R^{21}$ and $R^{22}$ are as defined above under the formula II and are preferably as defined above under the formula II1.

The liquid-crystal medium particularly preferably comprises one or more compounds selected from the group consisting of the compounds of the formulae III1 to III3:

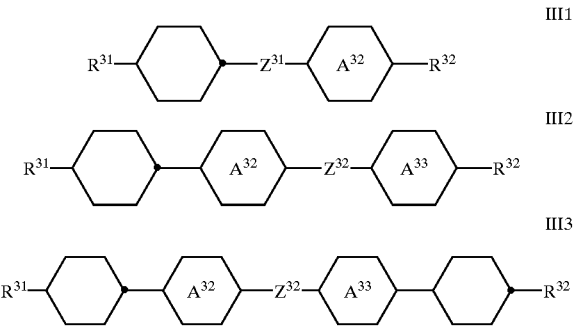

in which $R^{31}$, $R^{32}$, $Z^{31}$, $Z^{32}$,

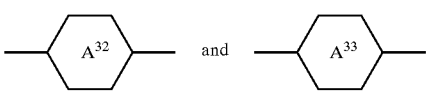

are each as defined above under the formula III.

The liquid-crystal medium particularly preferably comprises one or more compounds selected from the group consisting of the compounds of the formulae III1a to III1d, III2a to III2e, III3a to III3c and III4a:

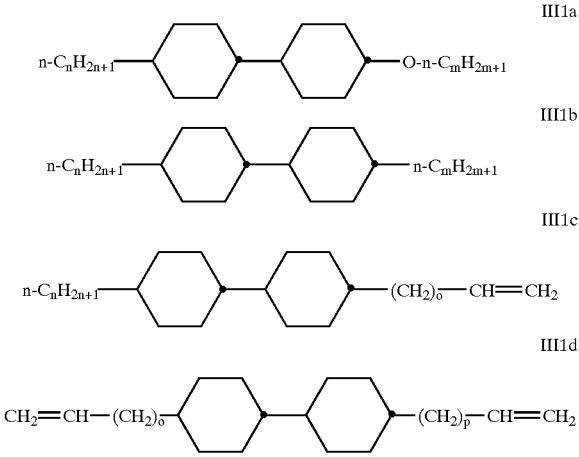

in which n and m are each, independently of one another, from 1 to 5, and o and p are each, both independently thereof and independently of one another, from 0 to 3,

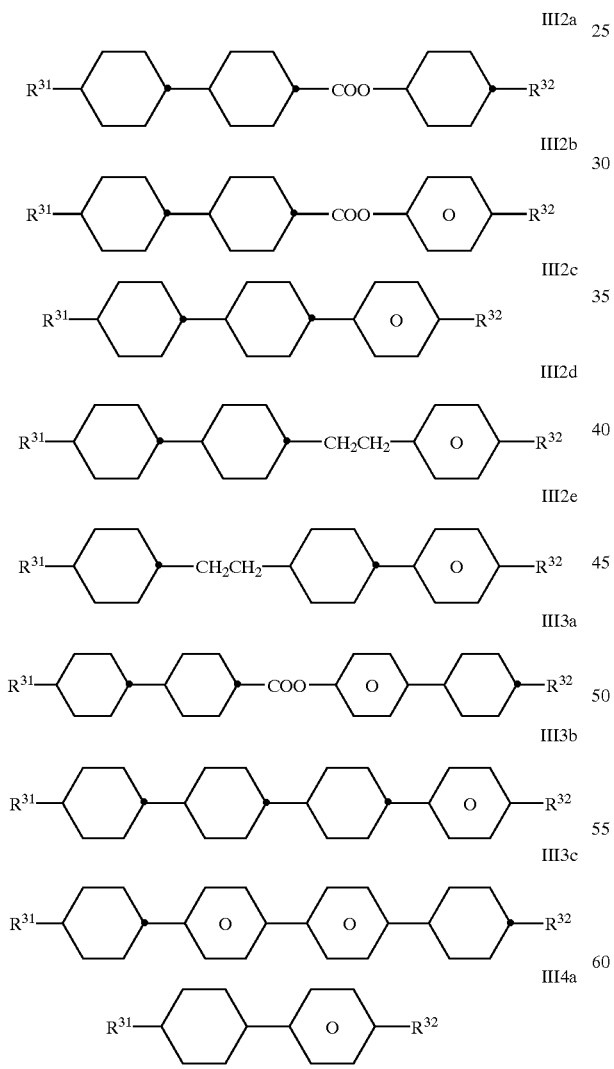

in which $R^{31}$ and $R^{33}$ are each as defined above under the formula III1, and the phenyl rings may optionally be fluorinated, but not in such a way that the compounds are identical to those of the formula II and their subformulae. $R^{31}$ is preferably n-alkyl having 1 to 5 carbon atoms, particularly preferably having 1 to 3 carbon atoms, and $R^{32}$ is preferably n-alkyl or n-alkoxy having 1 to 5 carbon atoms or alkenyl having 2 to 5 carbon atoms. Of these, particular preference is given to compounds of the formulae III1a to III1d.

In a preferred embodiment, the liquid-crystal media according to the invention comprise in total, based on the mixture as above, from 40% to 90% of compounds of the formula I, from 5% to 40% of compounds of the formula II and from 0% to 40% of compounds of the formula III.

The term compounds here means both one and a plurality of compounds. The individual compounds here are employed in concentrations of from 1% to 30%, preferably from 2% to 30%, particularly preferably from 4% to 16%.

In a preferred embodiment, the liquid-crystal media particularly preferably comprise in total
from 50% to 70% of compounds of the formula I,
from 5% to 30% of compounds of the formula II and
from 10% to 40% of compounds of the formula III.

In this embodiment, the liquid-crystal media very particularly preferably comprise in total
from 52% to 65% of compounds of the formula I,
from 10% to 25% of compounds of the formula II and
from 15% to 35% of compounds of the formula III.

In a particularly preferred embodiment, which may be identical, and preferably is identical, to the preferred embodiments described above for the preferred concentration ranges, the liquid-crystal media comprise
one or more compounds of the formula I1a and/or
one or more compounds of the formula I1b, and
one or more compounds of the formula III1a and/or
one or more compounds of the formula III1c the latter alternative being preferred, and
one or more compounds selected from the group consisting of the compounds of the formulae III1a to III1c and/or
one or more compounds selected from the group consisting of the compounds of the formulae III2 and III3, and
one or more compounds selected from the group consisting of the compounds of the formulae I1c to I1e, preferably Ic, and/or
one or more compounds selected from the group consisting of the compounds of the formulae I4a to I4e, preferably from the group consisting of the formulae I4b and I4e, particularly preferably both of the formula I4b and also I4e, and
one or more compounds of the formula II, preferably selected from the group of compounds of the formulae II1a and II1c.

Particularly preferred liquid-crystal media here are those which comprise
one or more compounds of the formula I1a, in particular, in each case per compound, in concentrations of from 6% to 14%,
one or more compounds of the formula I1b, in particular, in each case per compound, in concentrations of from 4% to 18%,
one or more compounds of the formula III1a, in particular, in each case per compound, in concentrations of from 3% to 10%,
one or more compounds of the formula III1c, in particular, in each case per compound, in concentrations of from 3% to 12%, preferably in each case at least one compound in which $R^{21}$ is alkyl having 1 to 3 carbon atoms and $R^{22}$ is alkoxy having 1 to 3 carbon atoms, and in which $R^{23}$ is alkyl having 1 to 3 carbon atoms and $R^{23}$ is alkyl having 1 to 3 carbon atoms, one or more compounds of the formulae III1a and/or III1c, in particular in concentrations of from 4% to 15% per compound, preferably in each case at least one compound of each of the formulae III1a and III1c, and one or more compounds of the formula III2a.

The liquid-crystal media according to the invention preferably have nematic phases of in each case at least from −20° C. to 80° C., preferably from −30° C. to 80° C., very particularly preferably from −40° C. to 85° C. (≧90° C.). The term "having a nematic phase" here means firstly that no smectic phase and no crystallization are observed at low temperatures at the corresponding temperature, and secondly that no clearing occurs during heating from the nematic phase. The investigation at low temperatures is carried out in a flow viscometer at the corresponding temperature, and checked by storage in test cells having an appropriate layer thickness for electro-optical use, for at least 100 hours. At high temperatures, the clearing point is measured by conventional methods in capillaries.

The liquid-crystal media according to the invention are furthermore characterized by low optical anisotropy values. The birefringence values are less than or equal to 0.10, preferably less than or equal to 0.08, very particularly preferably less than or equal to 0.07.

In addition, the liquid-crystal media according to the invention have small threshold voltage values of less than or equal to 2.0 V, preferably less than or equal to 1.9 V, particularly preferably less than or equal to 1.7 V, very particularly preferably less than or equal to 1.5 V.

These preferred values for the individual physical properties are also maintained when in each case combined with one another. Thus, media according to the invention have, in particular, the following property combinations:

| | Phase | Δn | Threshold voltage/V |
|---|---|---|---|
| According to the invention | ≦−20 to ≧80 | ≦0.10 | ≦1.9 |
| Preferred | ≦−30 to ≧90 | ≦0.08 | ≦1.7 |
| Particularly preferred | ≦−40 to ≧80 | ≦0.07 | ≦1.5 | where, as in the entire application, "≦" means less than or equal to and "≧" means greater than or equal to.

For displays containing liquid crystals of negative Δε, in particular for ECB and particularly preferably for VAN displays, the liquid-crystal media preferably comprise in total from 0.5% to 38% of compounds of the formula I, from 20% to 95% of compounds of the formula II and from 5% to 50% of compounds of the formula III.

These liquid-crystal media particularly preferably comprise
from 1% to 15% of compounds of the formula I,
from 50% to 85% of compounds of the formula II and
from 10% to 40% of compounds of the formula III.

These liquid-crystal media very particularly preferably comprise
from 1% to 10% of compounds of the formula I,
from 60% to 80% of compounds of the formula II and
from 20% to 35% of compounds of the formula III.

Independently of the abovementioned amount limits for the compounds of the formulae II and III, compounds of the formula I are employed in these liquid-crystal media in concentrations of up to 7%, preferably up to 5%.

In a preferred embodiment, these liquid-crystal media comprise
one or more compounds of the formula I1c and
one or more compounds of the formula II1a and/or preferably
one or more compounds of the formula II1c, and
one or more compounds of the formulae III1c and/or III1d and/or
one or more compounds of the formula III1b and/or
one or more compounds of the formula III4a.

The abovementioned preferred concentration ranges particularly preferably also apply to this preferred combination of compounds.

These liquid-crystal media according to the invention of negative Δε have nematic phases from −20° C., to +70° C., preferably from −30° C. to +70° C., particularly preferably from −30° C. to +80° C.

Particular preference is given to media having the following property combination:

| | Phase | Δn | Freedericksz threshold/V |
|---|---|---|---|
| According to the invention | ≦−20 to ≧70 | ≦0.09 | ≦2.0 |
| Preferred | ≦−30 to ≧70 | ≦0.08 | ≦1.9 |
| Particularly preferred | ≦−40 to ≧80 | ≦0.075 | ≦1.9 |

In the present application, the term "dielectrically positive compounds" is taken to mean compounds having a Δε of >1.5, the term "dielectrically neutral compounds" is taken to mean compounds in which −1.5≦Δε≦1.5, and "dielectrically negative compounds" is taken to mean compounds in which Δε is <−1.5. The dielectric anisotropy of the compounds is determined here by dissolving 10% of the compounds in a liquid-crystalline host and determining the capacitance of this mixture at 1 kHz in at least one test cell each with a thickness of 10 μm and a homeotropic and homogeneous surface alignment. The measurement voltage is typically from 0.5 V to 1.0 V, but is always less than the capacitive threshold of the respective liquid-crystal mixture.

The host mixture used for dielectrically positive compounds is ZLI-4792 and that used for dielectrically neutral and dielectrically negative compounds is ZLI-3086, both from Merck KGaA, Germany. The values for the respective compounds to be investigated are obtained from the change in dielectric constants of the host mixture after addition of the compound to be investigated and extrapolation to 100% of the compound employed.

The term threshold voltage in the present application relates to the optical threshold for 10% relative contrast ($V_{10}$), unless explicitly stated otherwise.

However, in relation to the liquid-crystal mixtures of negative dielectric anisotropy, the term threshold voltage is used for the capacitive threshold voltage ($V_0$), also known as the Freedericksz threshold, unless explicitly stated otherwise.

All concentrations in this application, unless explicitly stated otherwise, are given in per cent by weight and relate to the corresponding mixture as a whole. All physical properties are and have been determined as described in "Merck Liquid Crystals, Physical Properties of Liquid Crystals", Status Nov. 1997, Merck KGaA, Germany, and apply to a temperature of 20° C., unless explicitly-stated otherwise. Δn is determined at 589 nm and Δ∈ at 1 kHz. The threshold voltages and the other electro-optical properties were determined in test cells produced at Merck KGaA, Germany, using white light in a commercial measuring instrument from Otsuka, Japan. To this end, cells were used, depending on Δn of the liquid crystals, with a thickness corresponding to the 1st Gooch and Tarry transmission minimum. The optical retardation d·Δn of the cells was thus about 0.50 μm. The cells were operated in so-called "normally white mode" with a polarizer transmission direction perpendicular to the respective adjacent rubbing directions. The characteristic voltages were all determined with perpendicular observation. The threshold voltage was given as $V_{10}$ for 10% relative contrast, the central limit voltage $V_{50}$ for 50% relative contrast and the saturation voltage $V_{90}$ for 90% relative contrast.

In the liquid-crystal media of negative dielectric anisotropy, the threshold voltage was determined as the capacitive threshold $V_0$ (also known as the Freedericksz threshold) in cells containing liquids which had been homeotropically aligned by lecithin.

The DC offset voltage (ΔV) is determined as follows: the test pixel is addressed using a TFT, and the voltage shift is measured. The following equation applies:

$$\Delta V = V_{gate} \cdot c_{gs}/(c_{gs}+c_{st}+c_{LC}),$$

where $c_{gs}$ denotes the parasitic capacitance between the gate and source, $c_{st}$ denotes the capacitance of the storage capacitor, $c_{LC}$ denotes the capacitance of the LC layer of the pixel, and $V_{gate}$ denotes the gate voltage.

The liquid-crystal media according to the invention may, if necessary, also comprise further additives and chiral dopants in conventional amounts. The amount of these additives employed is in total from 0% to 10%, based on the amount of mixture as a whole, preferably from 0.1% to 6%. The concentrations of the individual compounds employed are preferably from 0.1 to 3%. The concentration of these and similar additives is not taken into account when giving the concentrations and the concentration ranges of the liquid-crystal compounds in the liquid-crystal media.

The compositions consist of a plurality of compounds, preferably from 3 to 30, particularly preferably from 6 to 20, very particularly preferably from 10 to 16 compounds, which are mixed in a conventional manner. In general, the desired amount of the components used in lesser amount is dissolved in the components making up the principal constituent, expediently at elevated temperature. If the temperature selected is above the clearing point of the principal constituent, completion of the dissolution operation is particularly easily observed. However, it is also possible to prepare the liquid-crystal mixtures in other conventional ways, for example by using premixtures or from a so-called "multibottle system".

By means of suitable additives, the liquid-crystal phases according to the invention can be modified in such a way that they can be employed in any type of TN-AMD that has been disclosed hitherto.

The examples below serve to illustrate the invention without representing a limitation. In the examples, the melting point T (C,N), the transition from the smectic (S) to the nematic (N) phase T (S,N) and the clearing point T (N,I) of a liquid-crystal substance are given in degrees Celsius. The percentage data denote percent by weight.

Unless stated otherwise, all percentages above and below are per cent by weight, and the physical properties are the values at 20° C., unless explicitly stated otherwise.

All temperature values given in this application are °C. and all temperature differences are correspondingly difference degrees, unless explicitly stated otherwise.

In the present application and in the examples below, the structures of the liquid-crystal compounds are indicated by means of acronyms, the transformation into chemical formulae taking place in accordance with Tables A and B below. All radicals $C_nH_{2n+1}$ and $C_mH_{2m+1}$ are straight-chain alkyl radicals having n and m carbon atoms respectively. The coding in Table B is self-evident. In Table A, only the acronym for the parent structure is given. In individual cases, the acronym for the parent structure is followed, separated by a hyphen, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nmF | $C_nH_{2n+1}$ | $C_mH_{2m+1}$ | F | H |
| $nCF_3$ | $C_nH_{2n+1}$ | $CF_3$ | H | H |
| $nOCF_3$ | $C_nH_{2n+1}$ | $OCF_3$ | H | H |
| $nOCF_2$ | $C_nH_{2n+1}$ | $OCHF_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nAm | $C_nH_{2n+1}$ | $COOC_mH_{2m+1}$ | H | H |
| nF.Cl | $C_nH_{2n+1}$ | Cl | H | F |

TABLE A

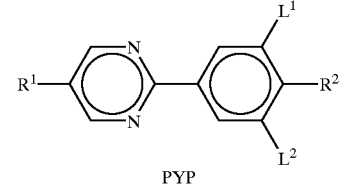

PYP

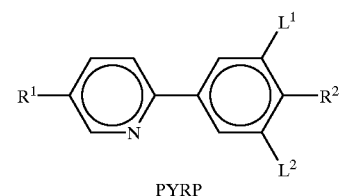

PYRP

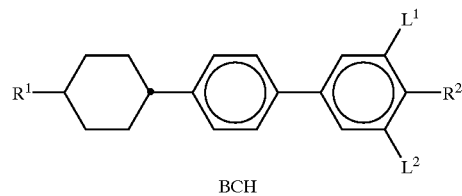

BCH

TABLE A-continued
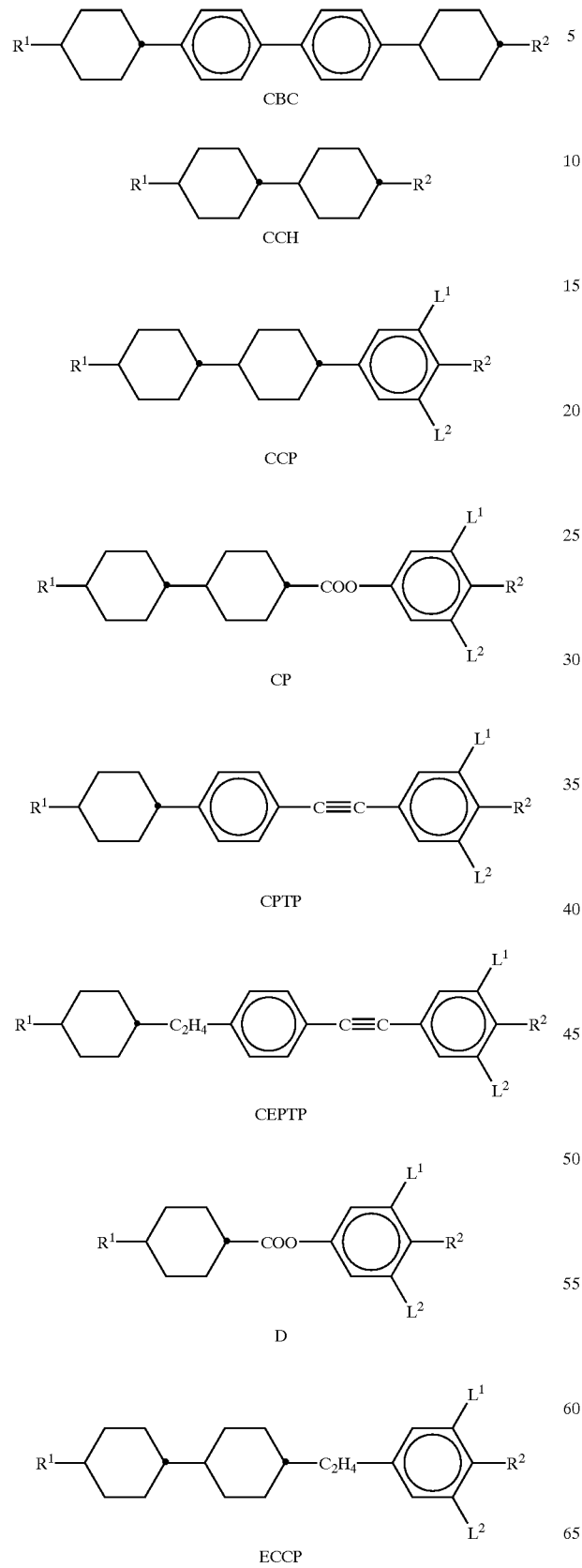
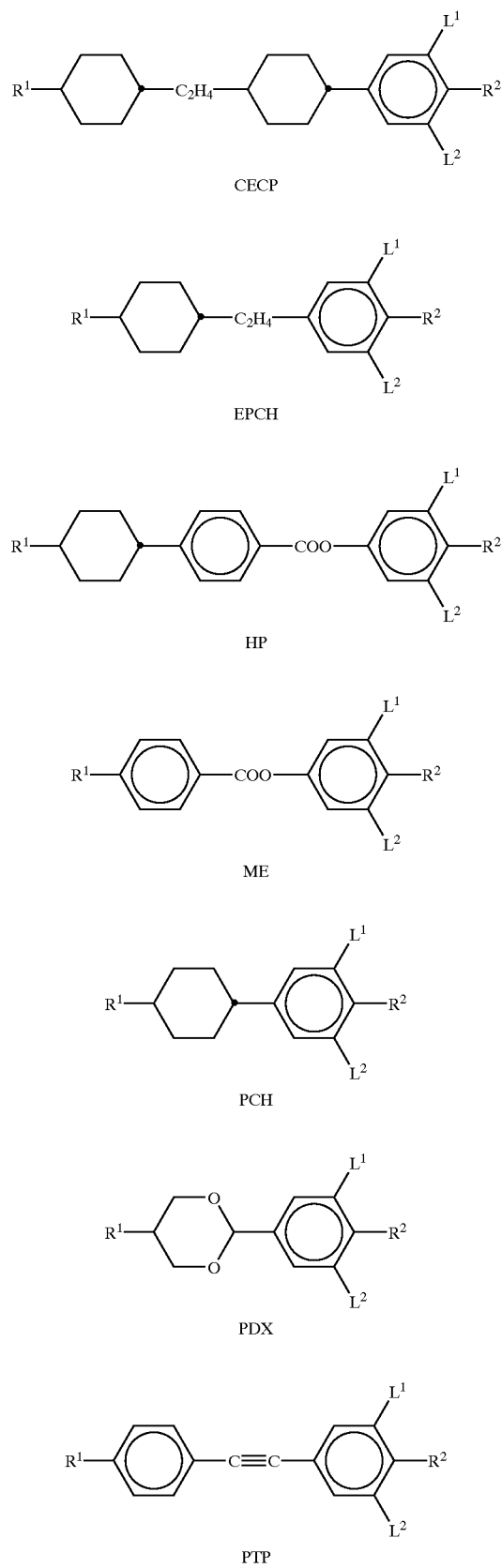

TABLE A-continued
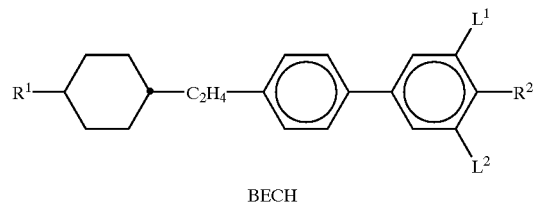
BECH
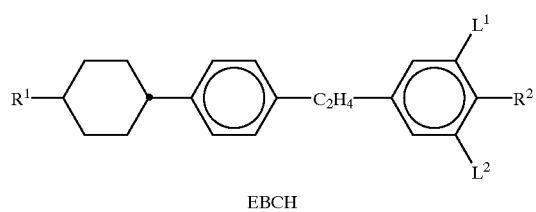
EBCH
CPC
TABLE A-continued
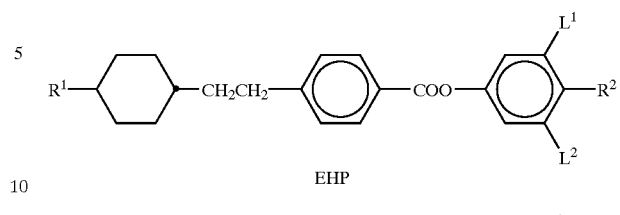
EHP
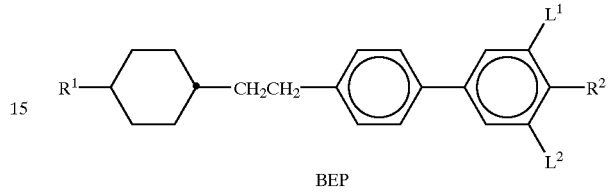
BEP
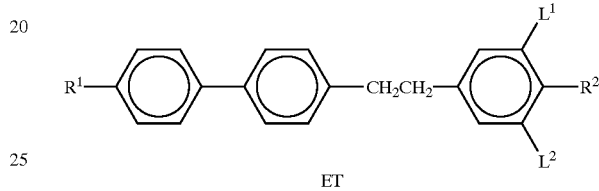
ET
TABLE B
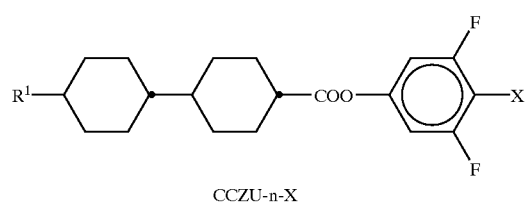
CCZU-n-X
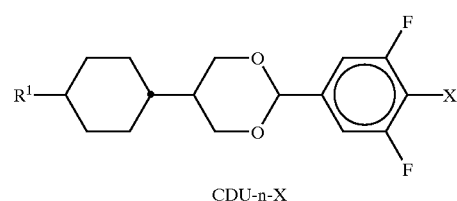
CDU-n-X
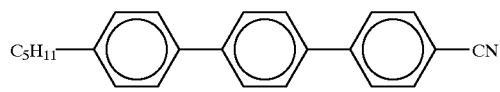
T15
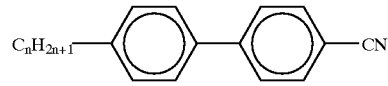
K3n
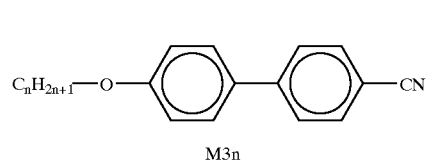
M3n TABLE B-continued
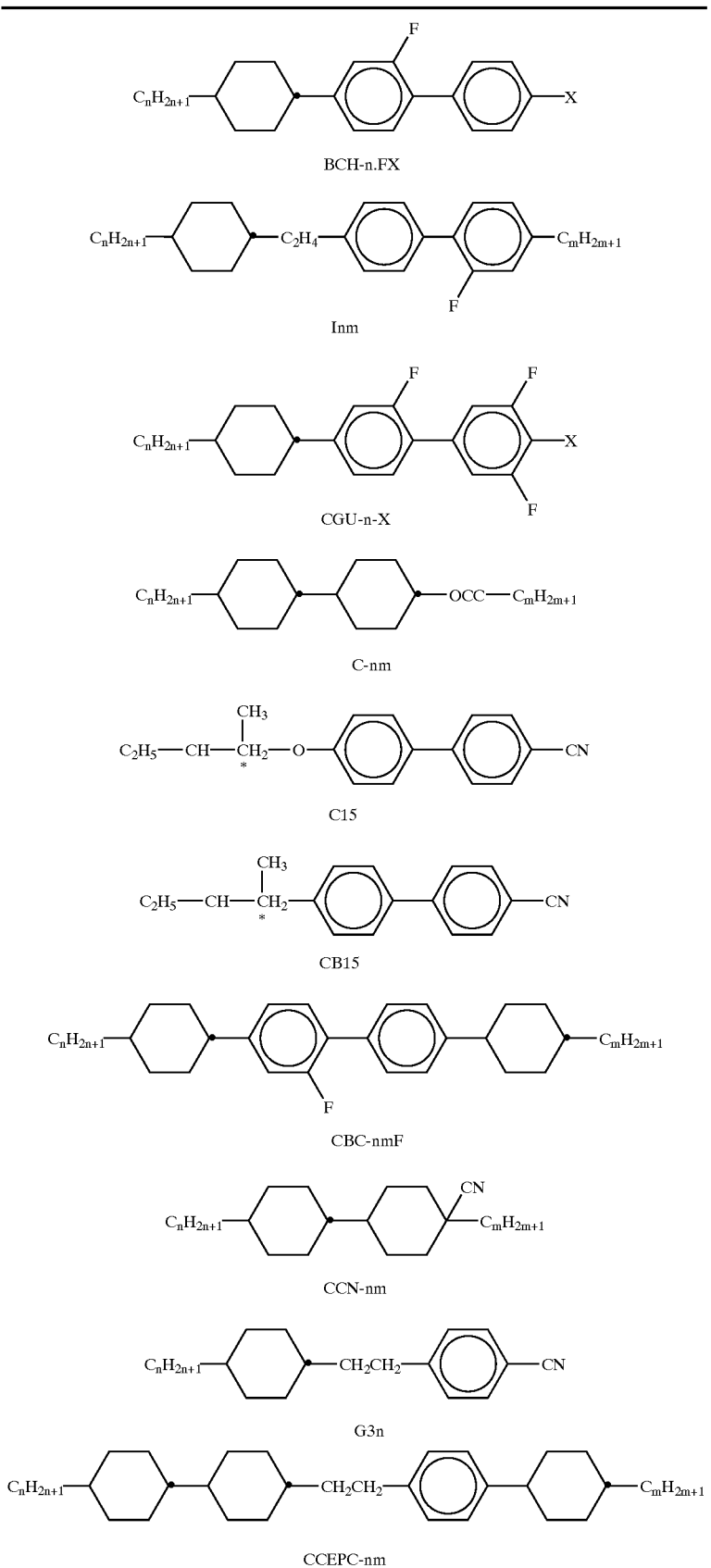

TABLE B-continued
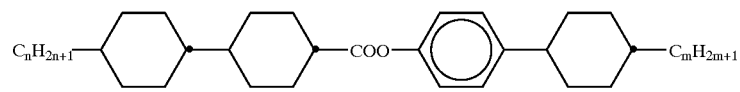
CCPC-nm
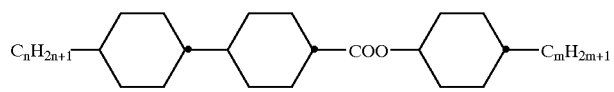
CH-nm
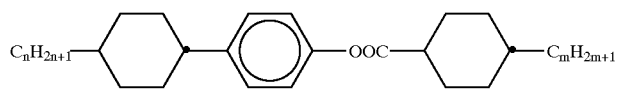
HD-nm
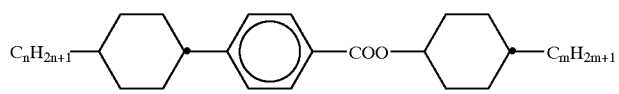
HH-nm
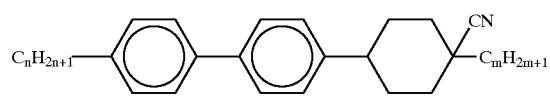
NCB-nm
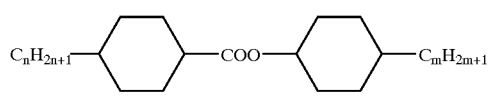
OS-nm
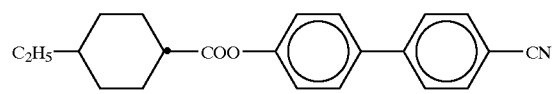
CHE
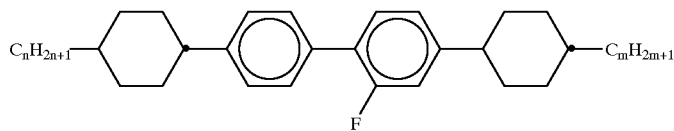
CBC-nmF
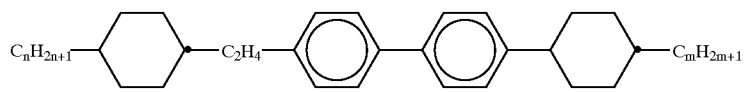
ECBC-nm
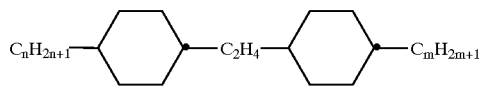
ECCH-nm TABLE B-continued
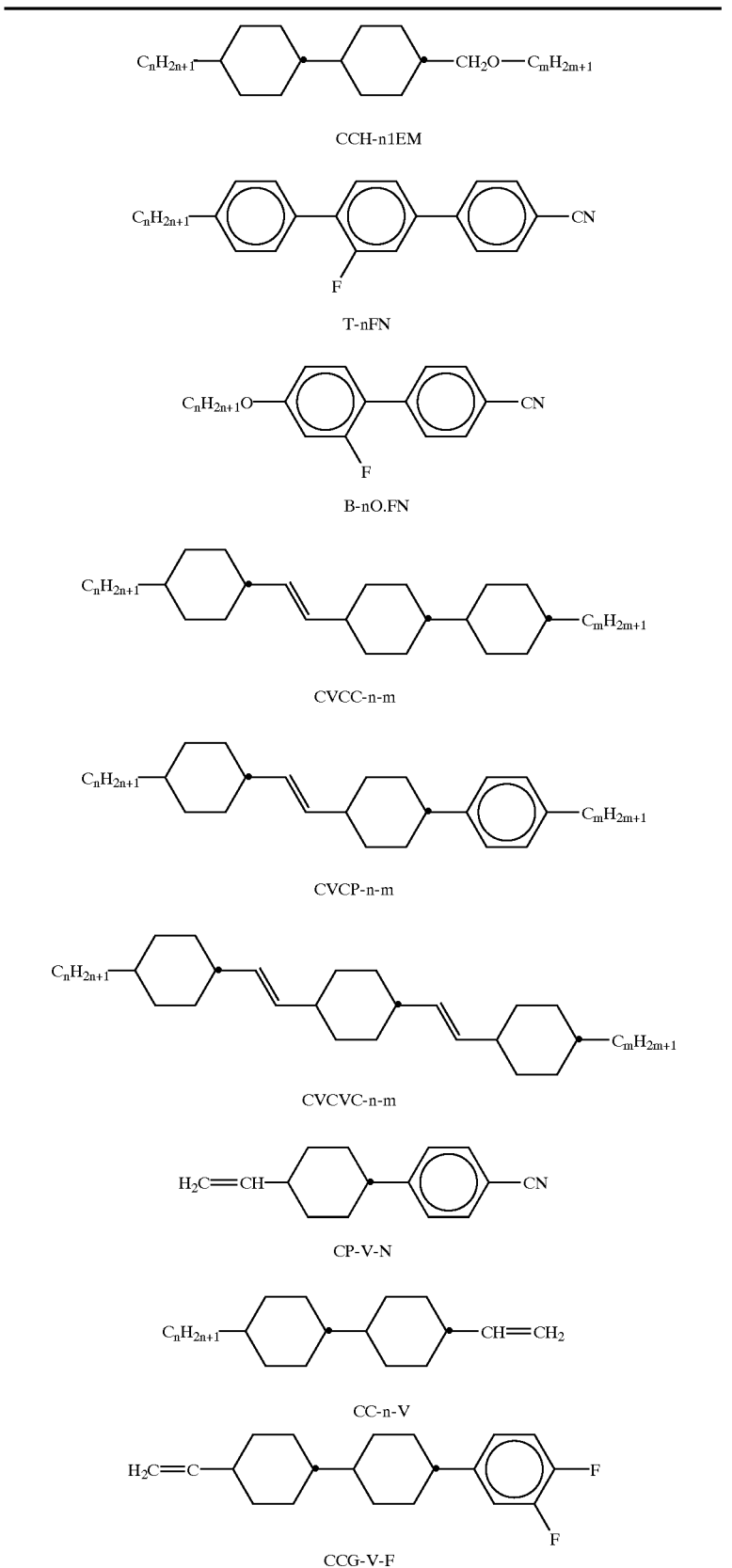

TABLE B-continued
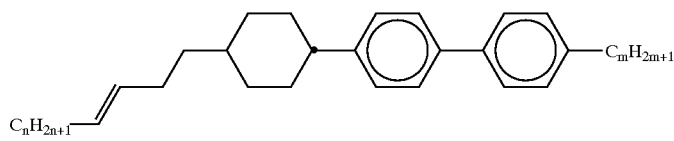
CCP-nV2-m
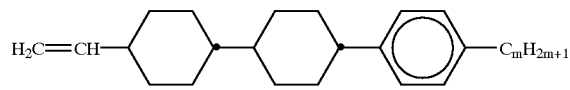
CCP-V-m
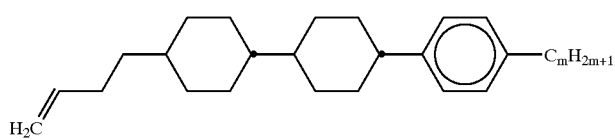
CCP-V2-m
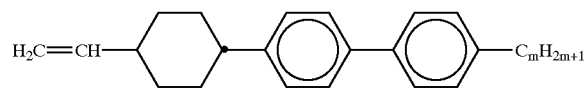
CCP-V-m
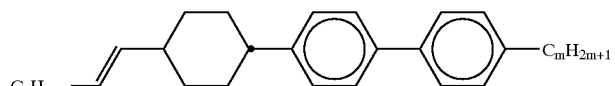
CCP-nV-m
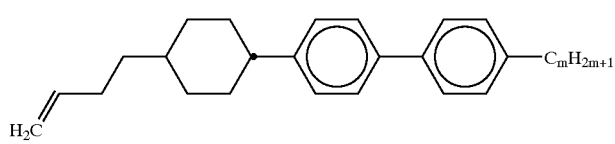
CPP-V2-m
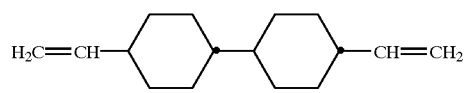
CC-V-V
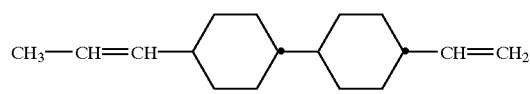
CC-1V-V
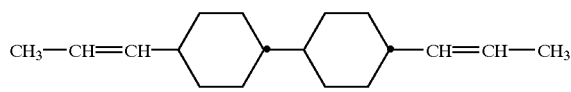
CC-1V-V1
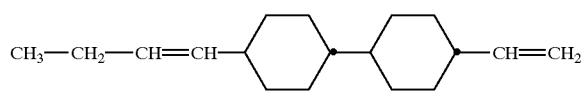
CC-2V-V TABLE B-continued

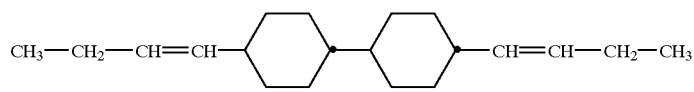

CC-2V-V2

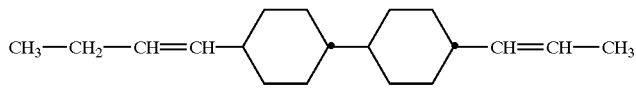

CC-2V-V1

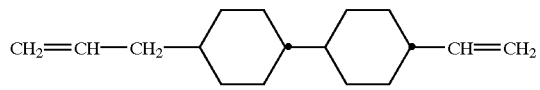

CC-V1-V

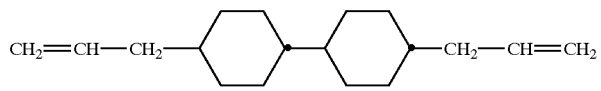

CC-V1-1V

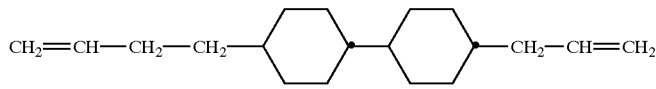

CC-V2-1V

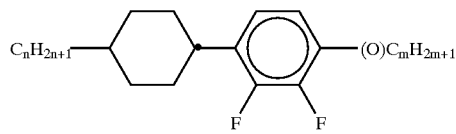

PCH-n(O)mFF

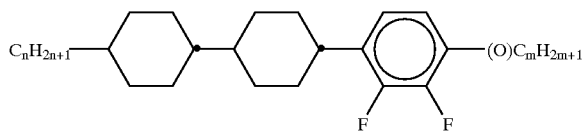

CCP-n(O)mFF

The examples below are intended to illustrate the invention without representing a limitation. Above and below, percentages are per cent by weight. All temperatures are given in degrees Celsius. Δn denotes the optical anisotropy (589 nm, 20° C.), Δε the dielectric anisotropy (1 kHz, 20° C.), H.R. the voltage holding ratio (at 100° C., after 5 minutes in an oven, 1 V), and $V_{10}$, $V_{50}$ and $V_{90}$ the threshold voltage, mid-grey voltage and saturation voltage respectively were determined at 20° C.

EXAMPLE 1

| Compound/abbreviation | Concentration/% | Properties |
|---|---|---|
| CCH-3O1 | 12.00 | Clearing point = 86.5° C. |
| CC-5-V | 6.00 | Transition (S,N) <−40° C. |

-continued

| Compound/abbreviation | Concentration/% | Properties |
|---|---|---|
| CH-33 | 4.00 | $V_{10}$ (20° C.) = 1.48 V |
| CH-35 | 4.00 | $V_{50}$ (20° C.) = 1.76 V |
| CCZU-2-F | 6.00 | $V_{90}$ (20° C.) = 2.21 V |
| CCZU-3-F | 16.00 | $d_v/d_T$ (0–40° C.) = 1.19 mV/° |
| CCZU-5-F | 6.00 | Δn (589 nm, 20° C.) = 0.0695 |
| CDU-2-F | 10.00 | |
| CDU-3-F | 12.00 | |
| CDU-5-F | 8.00 | |
| PCH-5O2FF | 5.00 | |
| CCP-3O2FF | 5.00 | |
| CCP-31FF | 6.00 | |
| | 100.00 | |

The liquid-crystal medium was introduced into a TN-AMD display with TFT addressing. This display had good contrast with low viewing-angle dependence and was substantially free from cross-talk between adjacent on and off pixels.

EXAMPLE 2

| Compound/abbreviation | Concentration/% | Properties |
|---|---|---|
| CCP-2F.F.F | 9.0 | Clearing point = 91.0° C. |
| CCP-3F.F.F | 10.0 | Transition (S,N) <-40° C. |
| CCP-3OCF3 | 8.0 | $\Delta n$ (20° C., 589 nm) = 0.1038 |
| CCP-5OCF3 | 8.0 | $\Delta \epsilon$ (20° C., 1 kHz) = 5.5 |
| BCH-3F.F.F | 12.0 | $\epsilon_\parallel$ (20° C., 1 kHz) = 11.4 |
| BCH-5F.F.F | 11.0 | $\epsilon_\perp$ (20° C., 1 kHz) = 5.9 |
| CGU-2-F | 6.0 | |
| PCH-302FF | 8.0 | |
| PCH-502FF | 8.0 | |
| CCP-302FF | 9.0 | |
| CCP-502FF | 8.0 | |
| CBC-33F | 3.0 | |
| | 100.00 | |

As in Example 1, the liquid-crystal medium was introduced into a TN-AMD display with TFT addressing. This display had good contrast with low viewing-angle dependence and was substantially free from cross-talk between adjacent on and off pixels.

Comparative Example 1

For comparison, the liquid-crystal medium disclosed in EP 0 406 468 of the following composition was prepared:

| Compound/abbreviation | Concentration/% | Properties |
|---|---|---|
| PCH-5F | 12.0 | Clearing point = 90.0° C. |
| PCH-6F | 10.0 | Transition (S,N) <-20° C. |
| PCH-7F | 10.0 | $\Delta n$ (20° C., 589 nm) = 0.0803 |
| CCP-3OCF3 | 13.0 | $\Delta \epsilon$ (20° C., 1 kHz) = 4.3 |
| CCP-5OCF3 | 12.0 | $\epsilon_\parallel$ (20° C., 1 kHz) = 7.2 |
| ECCP-3OCF3 | 11.0 | $\epsilon_\perp$ (20° C., 1 kHz) = 2.9 |
| ECCP-5OCF3 | 9.0 | |
| ECCP-3F.F | 13.0 | |
| CBC-33F | 3.0 | |
| CBC-53F | 4.0 | |
| CBC-55F | 3.0 | |
| | 100.00 | |

The liquid-crystal medium was introduced into a TN-AMD display as in Example 2. With similar properties regarding contrast and viewing-angle dependence, significantly more pronounced cross-talk was observed in the comparative experiment.

Furthermore, the capacitance of test cells having a layer thickness of 20 μm and electrode surface areas of 1 cm² with earthed protective ring electrodes were investigated. To do this, the voltage was increased in 0.1 V steps from 0.1 V to 1 V, then in 20 mV steps up to 2.0 V, then again in 0.1 V steps up to 5 V and subsequently in 1 V steps up to 20 V. The results are shown in FIG. 1.

FIG. 1 shows the capacitance of test cells filled with liquid-crystal mixtures as a function of the applied voltage. The solid diamonds (♦) show the results for the mixture of Example 2, the open triangles (Δ) those for Comparative Example 1. Up to a limiting voltage of the dielectric or Freedericksz's threshold, the capacitance of the test cells remains constant ($c_{off}$). The capacitance then increases with increasing voltage to a limit value ($c_{on}$). It is apparent that the mixture from Example 2 has a significantly better, i.e. smaller, $c_{on}/c_{off}$ ratio than the mixture of the comparative example, namely a $c_{on}/c_{off}$ of 1.9 compared with 2.3. It should be noted here that the capacitance axis in the figure must not begin at 0.

EXAMPLE 3

| Compound/abbreviation | Concentration/% | Properties |
|---|---|---|
| PCH-3O4FF | 12.00 | Clearing point = 70.5° C. |
| PCH-5O2FF | 12.00 | Transition (S,N) <-40° C. |
| PCH-5O4FF | 12.00 | $\Delta n$ (20° C., 589 nm) = 0.0813 |
| CCP-2O2FF | 11.00 | $n_o$ (20° C., 589 nm) = 1.4761 |
| CCP-3O2FF | 11.00 | $K_1$ (20° C.) = 13.0 pN |
| CCP-5O2FF | 10.00 | $K_3$ (20° C.) = 13.7 pN |
| CCP-2F.F.F | 2.00 | $V_o$ (20° C.) = $V_{Fr.}$ = 1.97 V |
| CC-5-V | 3.00 | d = 4 μm |
| CCH-34 | 5.00 | |
| CCH-35 | 5.00 | |
| CCPC-34 | 4.00 | |
| PCH-53 | 13.00 | |
| Σ | 100.00 | |

The liquid-crystal medium was prepared and investigated in a conventional manner. It was then introduced into a VAN display with TFT addressing. This display has very good contrast and virtually no viewing-angle dependence. In addition, it is practically free from cross-talk between adjacent pixels. In addition, no flicker occurs.

The offset voltage was determined as described above. At a gate voltage ($V_{gate}$) of 5 V (with $c_{gs}$=0.05 pF and with no storage capacitor), $\Delta V$=0.41 V.

Comparative Example 2

| Compound/abbreviation | Concentration/% | Properties |
|---|---|---|
| PCH-3O2FF | 16.00 | Clearing point = 71.0° C. |
| PCH-5O2FF | 14.00 | Transition (S,N) <-30° C. |
| CCP-3O2FF | 12.00 | $\Delta n$ (20° C., 589 nm) = 0.0822 |
| CCP-5O2FF | 11.00 | $n_o$ (20° C., 589 nm) = 1.5587 |
| CCP-21FF | 9.00 | $K_1$ (20° C.) = 13.6 pN |
| CCP-31FF | 8.00 | $K_3$ (20° C.) = 14.7 pN |
| CCH-34 | 8.00 | $V_o$ (20° C.) = $V_{Fr.}$ = 2.08 V |
| CCH-35 | 9.00 | d = 4 μm |
| PCH-53 | 7.00 | |
| PCH-3O1 | 6.00 | |
| Σ | 100.00 | |

The above liquid-crystal mixture was prepared and investigated analogously to the liquid-crystal mixtures from Example 3. This liquid-crystal mixture is dielectrically negative like that of Example 3. However, in contrast thereto, it contains no dielectrically positive compounds.

Although the liquid-crystal mixture of this Comparative Example 2 generally has similar properties to that of Example 3, it is inferior thereto in virtually all applicationally relevant properties, for example in contrast, viewing-angle dependence, in particular in the operating voltage (threshold voltage) and most clearly in the occurrence of cross-talk and flicker in VAN displays.

The offset voltage was determined as described in Example 3. At a gate voltage ($V_{gate}$) of 5 V (with $c_{gs}$=0.05 pF and with no storage capacitor), $\Delta V$=0.45 V.

EXAMPLE 4

| Compound/abbreviation | Concentration/% | Properties |
|---|---|---|
| CCP-3O2FF | 12.00 | Clearing point = 89.0° C. |
| CCP-5O2FF | 12.00 | Transition (S,N) <−30° C. |
| BCH-3F.F.F | 14.00 | $\Delta n$ (20° C., 589 nm) = 0.1622 |
| BCH-5F.F.F | 10.00 | $n_o$ (20° C., 589 nm) = 1.4902 |
| CGU-2-F | 16.00 | $\Delta\epsilon$ (20° C., 1 kHz) = 11.3 |
| CGU-3-F | 14.00 | $\epsilon_\perp$ (20° C., 1 kHz) = 6.3 |
| CGU-5-F | 14.00 | $d \cdot \Delta n$ = 0.55 μm |
| CCGU-3-F | 8.00 | $\lambda$ = 550 nm |
| | | $\phi$ = 90° S |
| | | $V_{10}$ (20° C.) = 1.270 |
| | | $V_{90}$ (20° C.) = 2.04 |
| Σ | 100.00 | |

EXAMPLE 5

| Composition | Concentration/% | Properties |
|---|---|---|
| CCP-2F.F.F | 9.0 | Clearing point = +91.0° C. |
| CCP-3F.F.F | 10.0 | $\Delta n$ = +0.1038 |
| CCP-3OCF3 | 8.0 | $n_o$ (589.3 nm, 20° C.) = 1.4808 |
| CCP-5OCF3 | 8.0 | $\Delta\epsilon$ (1 kHz, 20° C.) = 5.5 |
| BCH-3F.F.F | 12.0 | $\epsilon_\perp$ (1 kHz, 20° C.) = 5.9 |
| BCH-5F.F.F | 11.0 | $K_1$ (20° C.) = 12.1 pN |
| CGU-2-F | 6.0 | $K_3$ (20° C.) = 15.3 pN |
| PCH-3O2FF | 8.0 | $V_0$ (20° C.) = 1.57 V |
| PCH-5O2FF | 8.0 | |
| CCP-3O2FF | 9.0 | |
| CCP-5O2FF | 8.0 | |
| CBC-33F | 3.0 | |
| Σ | 100.0 | |

EXAMPLE 6

| Composition | Concentration/% | Properties |
|---|---|---|
| PCH-5O2FF | 6.0 | Clearing point = +90.0° C. |
| CCP-3O2FF | 10.0 | $\Delta n$ = +0.0919 |
| CCP-5O2FF | 10.0 | $n_o$ (589.3 nm, 20° C.) = 1.4794 |
| CCP-21FF | 8.0 | $\Delta\epsilon$ (1 kHz, 20° C.) = 4.2 |
| CCP-2OCF3 | 5.0 | $\epsilon_\perp$ (1 kHz, 20° C.) = 5.4 |
| CCP-3OCF3 | 2.0 | |
| CCP-2F.F.F | 8.5 | |
| CCP-3F.F.F | 8.5 | |
| CGU-2-F | 12.0 | |
| CGU-3-F | 10.0 | |
| CC-5-V | 13.5 | |
| CCH-35 | 3.5 | |
| CBC-33F | 3.0 | |
| Σ | 100.0 | |

EXAMPLE 7

| Composition | Concentration/% | Properties |
|---|---|---|
| PCH-5O2FF | 6.0 | Clearing point = +109.0° C. |
| CCP-3O2FF | 6.0 | $\Delta n$ = +0.0957 |
| CCP-5O2FF | 12.0 | $n_o$ (589.3 nm, 20° C.) = 1.4767 |
| CCP-21FF | 10.0 | $\Delta\epsilon$ (1 kHz, 20° C.) = 4.8 |
| CCP-31FF | 6.0 | $\epsilon_\perp$ (1 kHz, 20° C.) = 5.5 |
| CCP-2OCF3 | 4.0 | |
| CCP-3OCF3 | 4.0 | |
| CCP-4OCF3 | 6.0 | |
| CCP-5OCF3 | 6.0 | |
| CCP-2F.F.F | 8.0 | |
| CCP-3F.F.F | 8.0 | |
| CCP-5F.F.F | 4.0 | |
| CGU-3-F | 7.0 | |
| CGU-5-F | 10.0 | |
| CCH-35 | 3.0 | |
| Σ | 100.0 | |

EXAMPLE 8

| Composition | Concentration/% | Properties |
|---|---|---|
| PCH-5O2FF | 6.0 | Clearing point = +90.0° C. |
| CCP-3O2FF | 12.0 | $\Delta n$ = +0.0956 |
| CCP-5O2FF | 12.0 | $n_o$ (589.3 nm, 20° C.) = 1.4798 |
| CCP-21FF | 4.0 | $\Delta\epsilon$ (1 kHz, 20° C.) = 3.2 |
| CCP-2OCF3 | 6.0 | $\epsilon_\perp$ (1 kHz, 20° C.) = 5.5 |
| CCP-3OCF3 | 6.0 | $K_1$ (20° C.) = 13.4 pN |
| CCP-4OCF3 | 6.0 | $K_2$ (20° C.) = 6.5 pN |
| CCP-2F.F.F | 6.0 | $K_3$ (20° C.) = 16.8 pN |
| CCP-3F.F.F | 10.0 | |
| CGU-2-F | 10.0 | |
| CGU-3-F | 2.0 | |
| BCH-32F | 2.0 | |
| PCH-3O2 | 18.0 | |
| Σ | 100.0 | |

EXAMPLE 9

| Composition | Concentration/% | Properties |
|---|---|---|
| PCH-5O2FF | 6.0 | Clearing point = +91° C. |
| CCP-3O2FF | 8.0 | $\Delta n$ = +0.0955 |
| CCP-5O2FF | 12.0 | $n_o$ (589.3 nm, 20° C.) = 1.4791 |
| CCP-21FF | 6.0 | $\Delta\epsilon$ (1 kHz, 20° C.) = 4.9 |
| CCP-2OCF3 | 4.0 | $\epsilon_\perp$ (1 kHz, 20° C.) = 5.4 |
| CCP-3OCF3 | 6.0 | $K_1$ (20° C.) = 12.3 pN |
| CCP-4OCF3 | 6.0 | $K_2$ (20° C.) = 6.4 pN |
| CCP-2F.F.F | 8.0 | $K_3$ (20° C.) = 16.3 pN |
| CCP-3F.F.F | 8.0 | |
| CCP-5F.F.F | 6.0 | |
| CGU-3-F | 8.0 | |
| CGU-5-F | 10.0 | |
| PCH-3O2 | 12.0 | - |
| Σ | 100.0 | |

EXAMPLE 10

| Composition | Concentration/% | Properties |
|---|---|---|
| PCH-5O2FF | 6.0 | Clearing point = +91.0° C. |
| CCP-3O2FF | 10.0 | Δn = +0.0909 |
| CCP-5O2FF | 10.0 | $n_o$ (589.3 nm, 20° C.) = 1.4784 |
| CCP-21FF | 8.0 | Δε (1 kHz, 20° C.) = 3.7 |
| CCP-2OCF3 | 4.0 | $\epsilon_\perp$ (1 kHz, 20° C.) = 5.3 |
| CCP-3OCF3 | 6.0 | |
| CCP-4OCF3 | 6.0 | |
| CCP-2F.F.F | 8.0 | |
| CCP-3F.F.F | 9.0 | |
| CCP-5F.F.F | 6.0 | |
| CGU-3-F | 6.0 | |
| CGU-5-F | 10.0 | |
| PCH-53 | 8.0 | |
| CC-5-V | 3.0 | |
| Σ | 100.0 | |

EXAMPLE 11

| Composition | Concentration/% | Properties |
|---|---|---|
| PCH-5O2FF | 8.0 | Clearing point = +81.0° C. |
| CCP-3O2FF | 9.0 | Δn = +0.0907 |
| CCP-5O2FF | 9.0 | $n_o$ (589.3 nm, 20° C.) = 1.4790 |
| CCP-21FF | 7.0 | Δε (1 kHz, 20° C.) = 4.3 |
| CCP-2OCF3 | 3.0 | $\epsilon_\perp$ (1 kHz, 20° C.) = 5.3 |
| CCP-3OCF3 | 6.0 | |
| CCP-4OCF3 | 5.0 | |
| CCP-2F.F.F | 8.0 | |
| CCP-3F.F.F | 9.0 | |
| CCP-5F.F.F | 6.0 | |
| CGU-3-F | 6.0 | |
| CGU-5-F | 9.0 | |
| PCH-53 | 9.0 | |
| PCH-3O2 | 6.0 | |
| Σ | 100.0 | |

EXAMPLE 12

| Composition | Concentration/% | Properties |
|---|---|---|
| PCH-5O2FF | 5.0 | Clearing point = +81.3° C. |
| CCP-3O2FF | 6.0 | Δn = +0.0682 |
| CCP-5O2FF | 6.0 | $n_o$ (589.3 nm, 20° C.) = 1.4741 |
| CCH-3O1 | 8.0 | Δε (1 kHz, 20° C.) = 4.8 |
| CCH-5O1 | 4.0 | $\epsilon_\perp$ (1 kHz, 20° C.) = 4.6 |
| CC-5-V | 14.0 | |
| PCH-7F | 5.0 | |
| CCP-2F.F.F | 8.0 | |
| CCP-3F.F.F | 11.0 | |
| CCP-5F.F.F | 5.0 | |
| CCZU-2-F | 5.0 | |
| CCZU-3-F | 15.0 | |
| CCZU-5-F | 5.0 | |
| CH-33 | 1.5 | |
| CH-43 | 1.5 | |
| Σ | 100.0 | |

EXAMPLE 13

| Composition | Concentration/% | Properties |
|---|---|---|
| PCH-5O2FF | 6.0 | Clearing point = +90.0° C. |
| CCP-3O2FF | 12.0 | Δn = +0.0956 |
| CCP-5O2FF | 12.0 | $n_o$ (589.3 nm, 20° C.) = 1.4798 |
| CCP-21FF | 4.0 | Δε (1 kHz, 20° C.) = 3.2 |
| CCP-2OCF3 | 6.0 | $\epsilon_\perp$ (1 kHz, 20° C.) = 5.5 |
| CCP-3OCF3 | 6.0 | $K_1$ (20° C.) = 13.4 pN |
| CCP-4OCF3 | 6.0 | $K_2$ (20° C.) = 6.5 pN |
| CCP-2F.F.F | 6.0 | $K_3$ (20° C.) = 16.8 pN |
| CCP-3F.F.F | 10.0 | |
| CGU-2-F | 10.0 | |
| CGU-3-F | 2.0 | |
| BCH-32F | 2.0 | |
| PCH-3O2 | 18.0 | |
| Σ | 100.0 | |

EXAMPLE 14

| Composition | Concentration/% | Properties |
|---|---|---|
| PCH-5O2FF | 6.0 | Clearing point = +91.0° C. |
| CCP-3O2FF | 8.0 | Δn = +0.0955 |
| CCP-5O2FF | 12.0 | $n_o$ (589.3 nm, 20° C.) 1.4791 |
| CCP-21FF | 6.0 | Δε (1 kHz, 20° C.) = 4.9 |
| CCP-2OCF3 | 4.0 | $\epsilon_\perp$ (1 kHz, 20° C.) = 5.5 |
| CCP-3OCF3 | 6.0 | $K_1$ (20° C.) = 12.3 pN |
| CCP-4OCF3 | 6.0 | $K_2$ (20° C.) = 6.4 pN |
| CCP-2F.F.F | 8.0 | $K_3$ (20° C.) = 16.3 pN |
| CCP-3F.F.F | 8.0 | |
| CCP-5F.F.F | 6.0 | |
| CGU-3-F | 8.0 | |
| CGU-5-F | 10.0 | |
| PCH-3O2 | 12.0 | |
| Σ | 100.0 | |

What is claimed is:

1. A nematic liquid-crystal medium, comprising a) one or more dielectrically positive compound(s) of the formula I

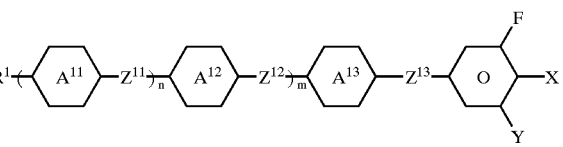

in which

R[1] is alkyl or alkoxy having 1 to 7 carbon atoms, alkoxyalkyl, alkenyl or alkenyloxy having 2 to 7 carbon atoms, Z[11], Z[12] and Z[13] are each, independently of one another, —CH$_2$—CH$_2$—, —CH═CH—, —C≡C—, —COO— or a single bond,

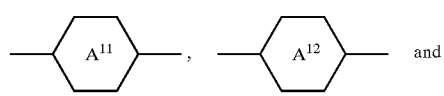

and

-continued

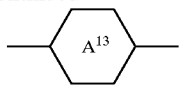

are each, independently of one another,

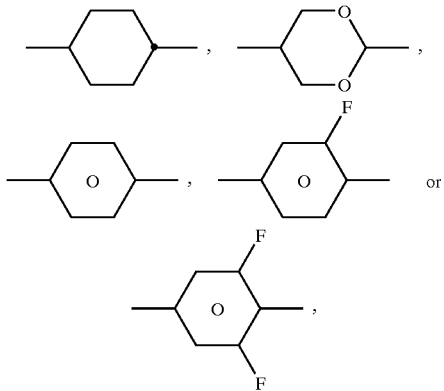

X is F, or $OCF_3$, where, in the case where X=F, Y is F, and in the case where X=$OCF_3$, Y is H or F, and n and m are each, independently of one another, 0 or 1;

b) one or more dielectrically negative compound(s) of the formula II

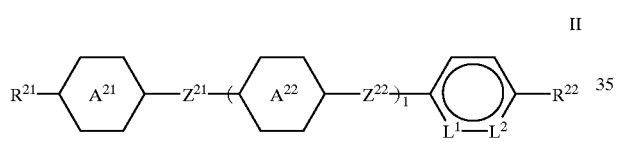

II in which $R^{21}$ and $R^{22}$ are each, independently of one another, as defined for $R^1$ under the formula I, $Z^{21}$ and $Z^{22}$ are each, independently of one another, as defined for $Z^{11}$ above under the formula I,

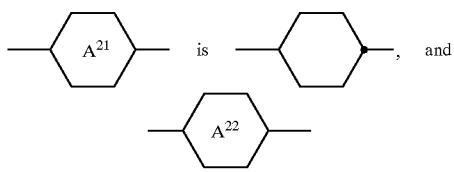

are each, independently of one another,

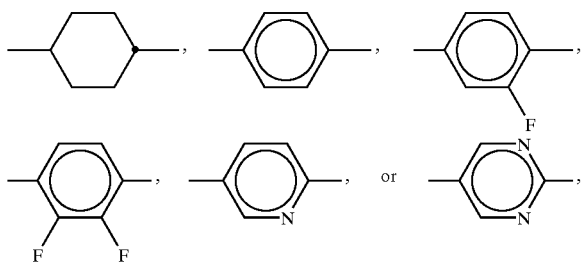

$L^1$ and $L^2$ are both C—F or one of the two is N and the other is C—F, and l is 0 or 1;

and optionally c) one or more dielectrically neutral compound(s) of the formula III

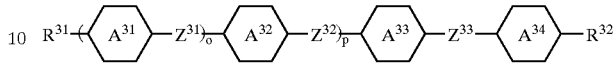

in which $R^{31}$ and $R^{32}$ are each, independently of one another, as defined for $R^1$ above under the formula I, and $Z^{31}$, $Z^{32}$ and $Z^{33}$ are each, independently of one another, —$CH_2CH_2$—, —$CH_2O$—, —$OCH_2$—, —$CF_2O$—, —$OCF_2$—, —COO— or a single bond, and, additionally, one of $Z^{31}$, $Z^{32}$ and $Z^{33}$ may also be —$CF_2CF_2$—,

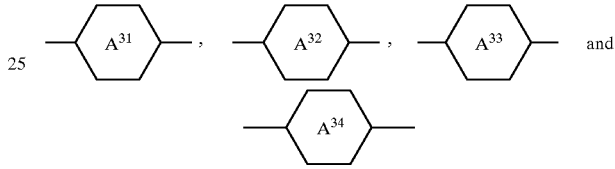

are each, independently of one another,

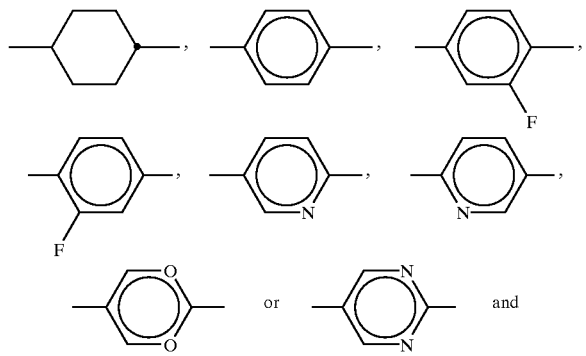

o and p, independently of one another, are 0 or 1, wherein the medium has a positive dielectric anisotropy of 3.2 or more, a birefringence, Δn, of less than or equal to 0.11, and the ratio of the dielectric anisotropies of the liquid-crystal medium parallel and perpendicular to the director is less than or equal to 1.93.

2. The liquid-crystal medium of claim 1 which comprises one or more compounds selected from the group of compounds of the formulae I1 to I4:

I1

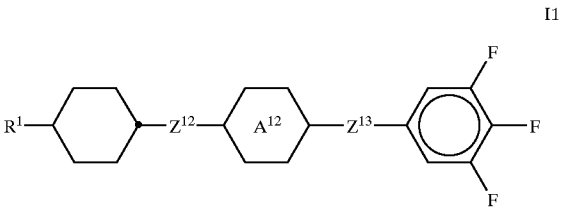

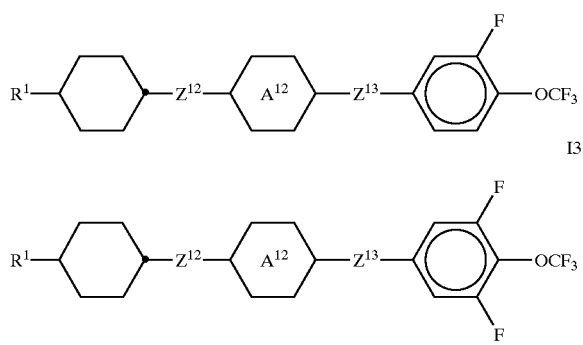

I2

I3 in which $R^1$, $Z^{12}$, $Z^{13}$ and

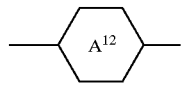

are each as defined in formula in claim 1.

3. The liquid-crystal medium of claim 1, which comprises one or more compounds of the formula II1

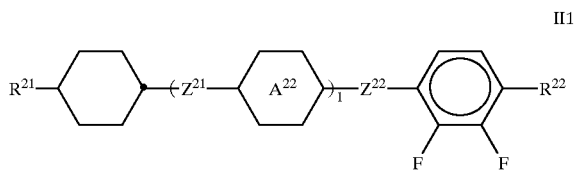

II1 in which $R^{21}$, $R^{22}$, $Z^{21}$, $Z^{22}$,

and 1 are as defined in claim 1.

4. The liquid-crystal medium of claim 1, which comprises at least one compound of the formula III.

5. The liquid-crystal medium of claim 1, which comprises one or more compounds selected from the group consisting of the compounds of the formulae III1 to III3

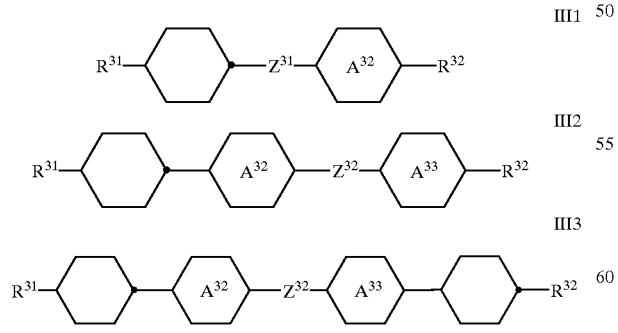

are each as defined for formula III in claim 1.

6. The liquid-crystal medium of claim 1, which comprises one or more compounds selected from the group consisting of the compounds of the formulae III1a to III1d

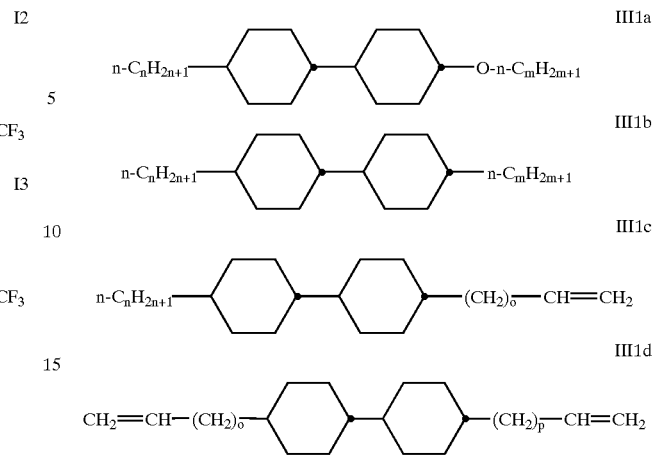

in which n and m are each, independently of one another, from 1 to 5, and o and p are each, both independently thereof and from one another, from 0 to 3.

7. The liquid-crystal medium of claim 1, which comprises in total from 50% to 70% of compounds of the formula I,
from 5% to 30% of compounds of the formula II and
from 10% to 40% of compounds of the formula III.

8. An electro-optical display comprising a liquid-crystal medium of claim 1.

9. The display of claim 8, which is an active matrix display having a matrix of three-pole active switches.

10. The liquid-crystal medium of claim 2, which comprises one or more compounds of the formula II1

II1

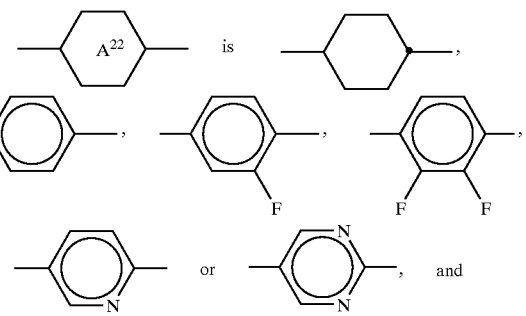

in which $R^{21}$ and $R^{22}$ are each, independently of one another, alkyl or alkoxy having 1 to 7 carbon atoms, alkoxyalkyl, alkenyl or alkenyloxy having 2 to 7 carbon atoms, $Z^{21}$ and $Z^{22}$ are each, independently of one another, —CH$_2$—CH$_2$—, —CH=CH—, —C≡C—, —COO— or a single bond, 1 is 0 or 1.

11. The liquid-crystal medium of claim 2, which comprises at least one compound of the formula III.

12. The liquid-crystal medium of claim 1, wherein the birefringence of the medium is 0.1038 or less.

13. The liquid-crystal medium of claim 1, wherein the birefringence of the medium is 0.10 or less.

14. The liquid-crystal medium of claim 1, wherein the birefringence of the medium is 0.08 or less.

15. The liquid-crystal medium of claim 1, wherein the medium exhibits a nematic phase at from −20° C. to 80° C.

16. The liquid-crystal medium of claim 1, wherein the threshold voltage measured at 20° C. and d·Δn of 0.50 μm is 1.9 V or less.

17. The liquid-crystal medium of claim 1, wherein the threshold voltage measured at 20° C. and d·Δn of 0.50 μm is 1.7 V or less.

18. The liquid-crystal medium of claim 1, wherein the threshold voltage measured at 20° C. and d·Δn of 0.50 μm is 1.5 V or less.

19. The liquid-crystal medium of claim 2, wherein the threshold voltage measured at 20° C. and d·Δn of 0.50 μm is 1.9 V or less.

20. The liquid-crystal medium of claim 2, wherein the threshold voltage measured at 20° C. and d·Δn of 0.50 μm is 1.7 V or less.

21. The liquid-crystal medium of claim 2, wherein the threshold voltage measured at 20° C. and d·Δn of 0.50 μm is 1.5 V or less.

22. The liquid-crystal medium of claim 7, wherein the threshold voltage measured at 20° C. and d·Δn of 0.50 μm is 1.9 V or less.

23. The liquid-crystal medium of claim 7, wherein the threshold voltage measured at 20° C. and d·Δn of 0.50 μm is 1.7 V or less.

24. The liquid-crystal medium of claim 7, wherein the threshold voltage measured at 20° C. and d·Δn of 0.50 μm is 1.5 V or less.

25. The liquid-crystal medium of claim 1, wherein the ratio of the dielectric anisotropies of the medium parallel and perpendicular to the director is equal to or less than 1.81.

26. The liquid-crystal medium of claim 1, wherein the ratio of the dielectric anisotropies of the medium parallel and perpendicular to the director is equal to or less than 1.70.

* * * * *

UNITED STATES PATENT AND TRADEMARK OFFICE
CERTIFICATE OF CORRECTION

PATENT NO. : 6,929,832 B2  
APPLICATION NO. : 09/465006  
DATED : August 16, 2005  
INVENTOR(S) : Michael Heckmeier Page 1 of 1

It is certified that error appears in the above-identified patent and that said Letters Patent is hereby corrected as shown below:

Column 36, line 50 reads
" 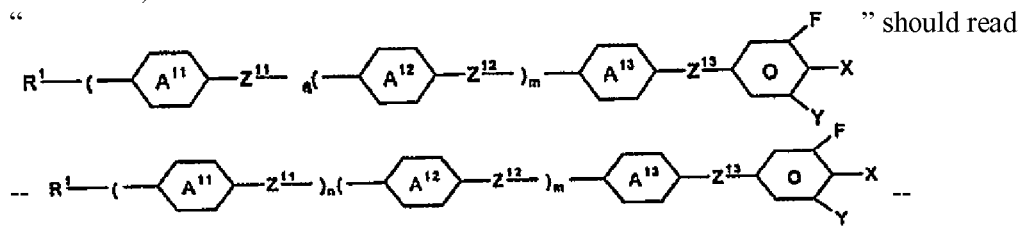 " should read

Column 38, line 10 reads
" 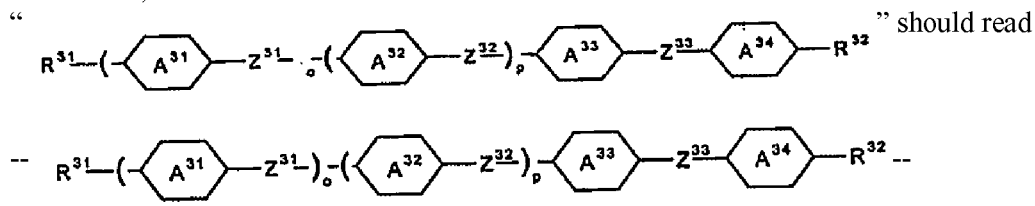 " should read

Column 38, line 45 reads " 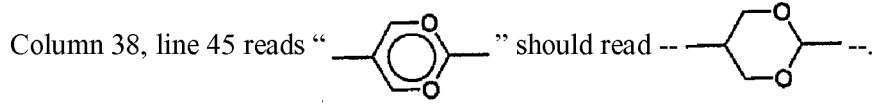 " should read --

Signed and Sealed this

First Day of May, 2007

JON W. DUDAS  
*Director of the United States Patent and Trademark Office*